US006846493B2

(12) United States Patent
Pugh et al.

(10) Patent No.: US 6,846,493 B2
(45) Date of Patent: Jan. 25, 2005

(54) SYNTHETIC BIOMATERIAL COMPOUND OF CALCIUM PHOSPHATE PHASES PARTICULARLY ADAPTED FOR SUPPORTING BONE CELL ACTIVITY

(75) Inventors: Sydney M. Pugh, Glennburnie (CA); Timothy J. N. Smith, Kingston (CA); Michael Sayer, Kingston (CA); Sarah Dorthea Langstaff, Kingston (CA)

(73) Assignee: Millenium Biologix Inc., Kingston (CA)

( * ) Notice: Subject to any disclaimer, the term of this patent is extended or adjusted under 35 U.S.C. 154(b) by 439 days.

(21) Appl. No.: 10/142,151

(22) Filed: May 10, 2002

(65) Prior Publication Data

US 2003/0003160 A1 Jan. 2, 2003

Related U.S. Application Data

(63) Continuation-in-part of application No. 09/971,148, filed on Oct. 4, 2001, now Pat. No. 6,585,992, which is a division of application No. 09/044,749, filed on Mar. 19, 1998, now Pat. No. 6,323,146, which is a continuation-in-part of application No. 09/029,872, filed as application No. PCT/CA96/00585 on Aug. 30, 1996, which is a continuation-in-part of application No. 08/576,238, filed on Dec. 21, 1995, now abandoned

(60) Provisional application No. 60/003,157, filed on Sep. 1, 1995.

(51) Int. Cl.$^7$ .............................................. A61L 27/00
(52) U.S. Cl. .......................... 424/423; 501/1; 501/123; 106/35; 623/23.61; 623/26.56; 423/306; 423/307; 423/308; 423/311; 423/312; 423/314; 423/315; 423/316
(58) Field of Search .............................. 424/423; 501/1, 501/123; 106/35; 623/23.61, 26.56; 423/306, 307, 308, 311, 312, 314, 315, 316

(56) References Cited

U.S. PATENT DOCUMENTS

| | | | |
|---|---|---|---|
| 4,503,157 A | 3/1985 | Hatahira | |
| 4,861,733 A | 8/1989 | White | |
| 4,871,578 A | 10/1989 | Adam et al. | |
| 4,983,182 A | 1/1991 | Kijima et al. | |
| 4,988,362 A | 1/1991 | Toriyama et al. | |
| 4,990,163 A | 2/1991 | Ducheyne et al. | |
| 5,011,495 A | 4/1991 | Hollinger | |
| 5,034,352 A | 7/1991 | Vit et al. | |
| 5,232,878 A | 8/1993 | Kasuga et al. | |
| 5,728,395 A | 3/1998 | Ohtsuka et al. | |
| 6,090,732 A | 7/2000 | Ito et al. | |

FOREIGN PATENT DOCUMENTS

| | | |
|---|---|---|
| FR | 2664501 | 1/1992 |
| GB | 2 316 940 A | 3/1998 |
| JP | 8-165216 | 6/1996 |
| WO | WO 91/17965 | 11/1991 |
| WO | WO 94/26882 | 11/1994 |
| WO | WO 95/32008 | 11/1995 |
| WO | WO 97/09286 | 3/1997 |
| WO | WO 98/08773 | 3/1998 |

OTHER PUBLICATIONS

Shimizu et al., "The effect of substrate composition and condition on resorption by isolated osteoclasts", Bone and Mineral, 6, pp. 261–275 (1989).

Jones et al., "The resorption of biological and non–biological substrates by cultured avian and mammalian osteoclasts," Anat. Embryol, 170:247–256 (1984).

Kerby et al., "Derivation of Osteoclasts from Hematopoietic Colony–Forming Cells in Culture," Journal of Bone and Mineral Research, vol. 7, No. 3, pp. 353–362 (1992).

Amano et al., "An Assay System Utilizing Devitalized Bone For Assessment of Differentiation of Osteoclast Progenitors," Journal of Bone and Mineral Research, vol. 7, No. 3, pp. 321–328 (1992).

Chambers et al., "Failure of Cells of the Mononuclear Phagocyte Series to Resorb Bone," Calcif. Tissue Intl., 36:556–558 (1984).

Chambers et al., "Resorption of Bone by Isolated Rabbit Osteoclasts," J. Cell Sci., 66, pp. 383–399 (1984).

Boyde et al., "Resorption of Dentine by Isolated Osteoclasts in vitro," British Dental Journal, 156, pp. 216–220 (1984).

Boyer et al., "Synthesis of phosphate–silicate apatites at atmospheric pressure," Solid State Ionics, 95, pp. 121–129, 1997.

Ruys, "Silicone–Doped Hydroxyapatite", J. Aust. Ceram. Soc. 29(1/2), p. 71–80, 1993.

Layrolle et al, "Sol–Gel Synthesis of Zinc Containing Calcium Phosphate Biomaterials", Phosphorus Research Bull. vol. 6, pp. 63–66, 1996.

Bigi et al, "Isomorphous Substitutions In B–Tricalcium–Phosphate: The Different Effects of Zinc and Strontium", Jour. Inorg. Biochem., vol. 66, pp. 259–265, 1997.

*Primary Examiner*—Jean C. Witz
(74) *Attorney, Agent, or Firm*—Sim & McBurney; Lola A. Bartoszewicz

(57) ABSTRACT

The present invention is directed to a synthetic biomaterial compound based on stabilized calcium phosphates and more particularly to the molecular, structural and physical characterization of this compound. The compound comprises calcium, oxygen and phosphorous, wherein at least one of the elements is substituted with an element having an ionic radius of approximately 0.1 to 1.1 Å. The knowledge of the specific molecular and chemical properties of the compound allows for the development of several uses of the compound in various bone-related clinical conditions.

11 Claims, 24 Drawing Sheets

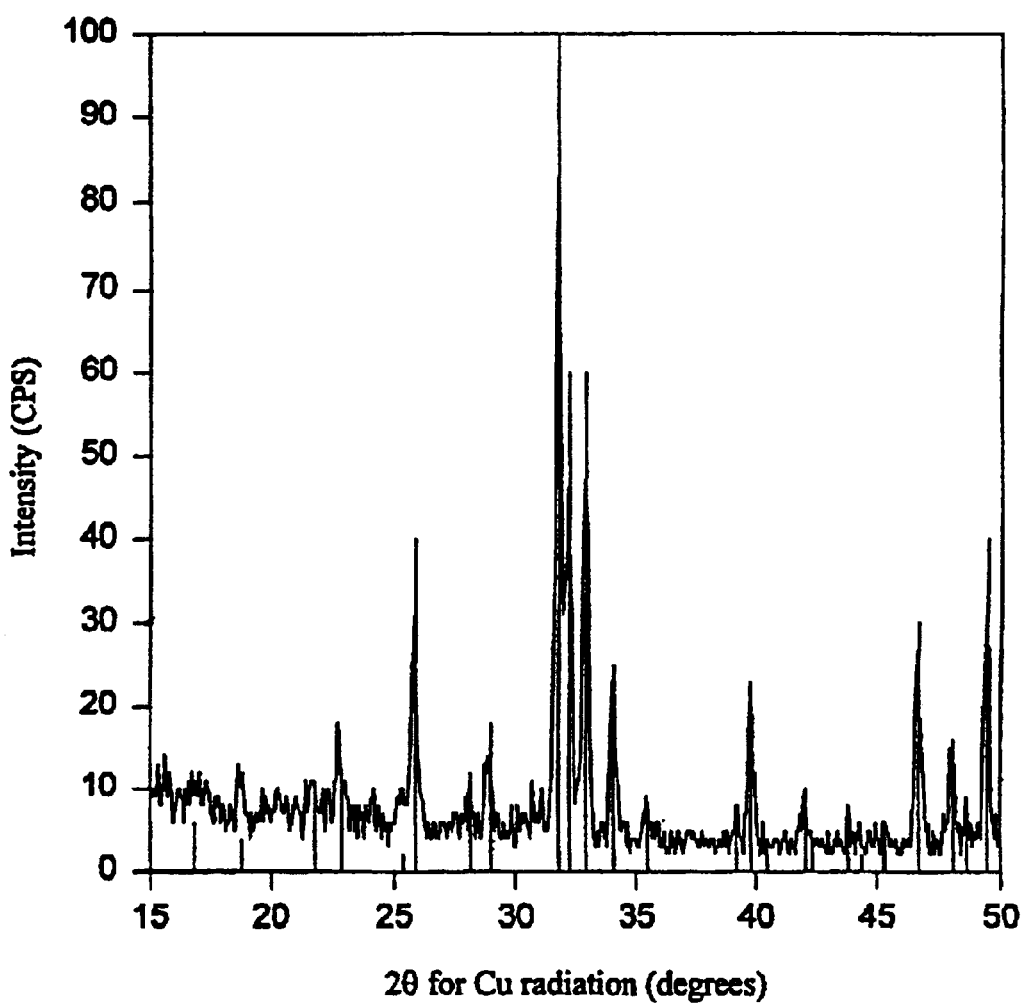
Figure 1: X-Ray Diffraction Spectrum (θ-2θ) of powder prepared from the Ca-P colloid with no introduced additives and sintered at 1000°C. Overlay of JCPDS File #9-432 (HA).

Figure 2: Glancing Angle X-Ray Diffraction Spectra of a thin film of the Ca-P colloid sintered on quartz at 1000°C.
(a) Overlay of JCPDS#9-348 (α-TCP).
(b) Overlay of JCPDS#9-432 (HA).
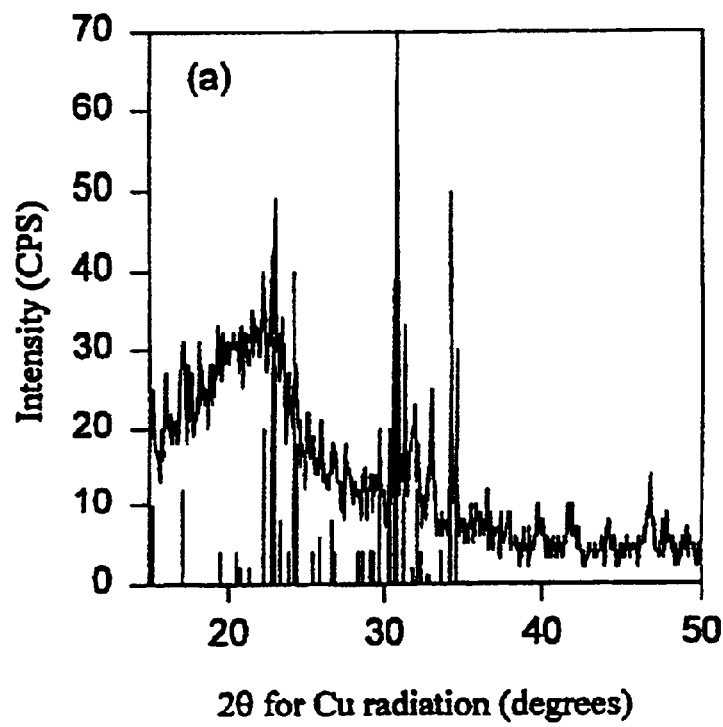
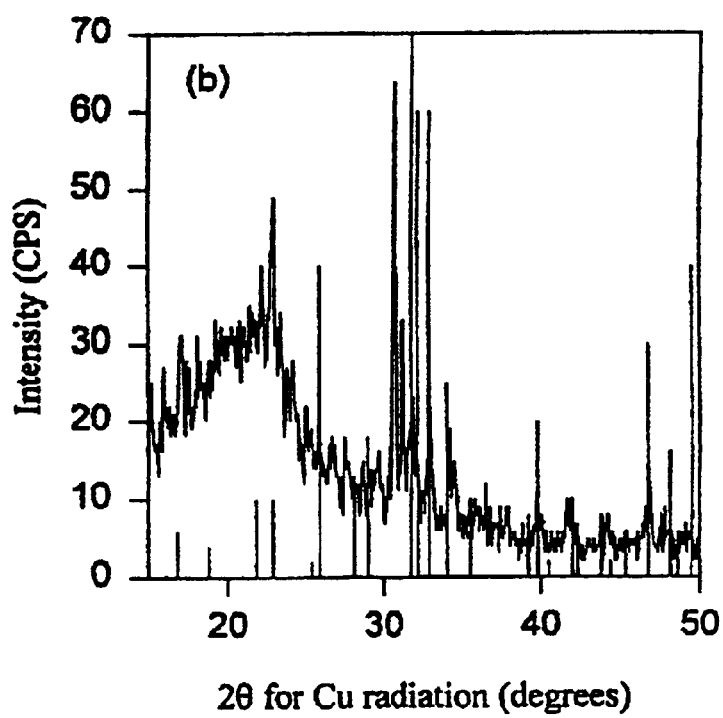

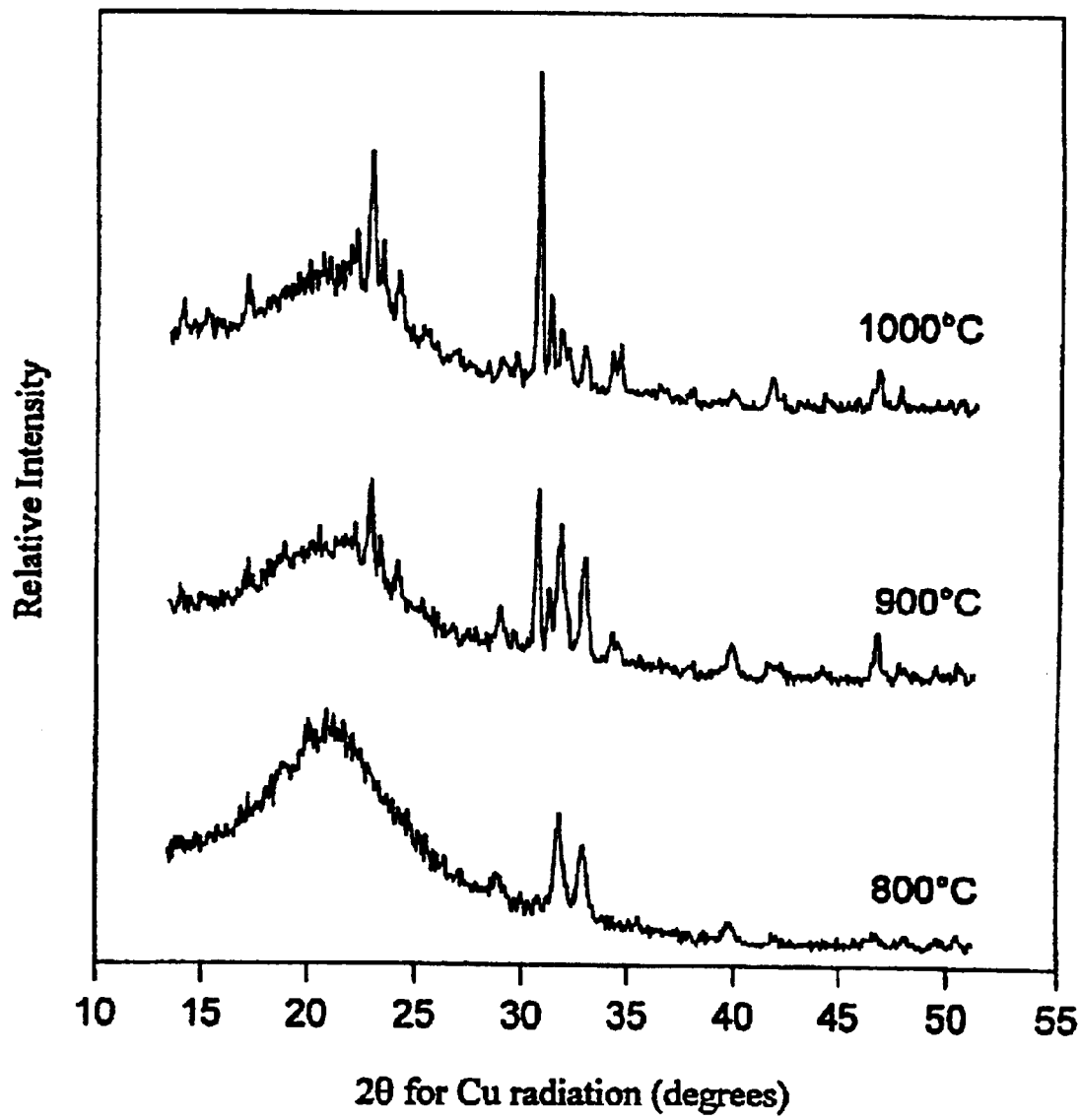
Figure 3: Glancing Angle X-Ray Diffraction Spectra illustrating the effect of sintering temperature on thin film phase composition.

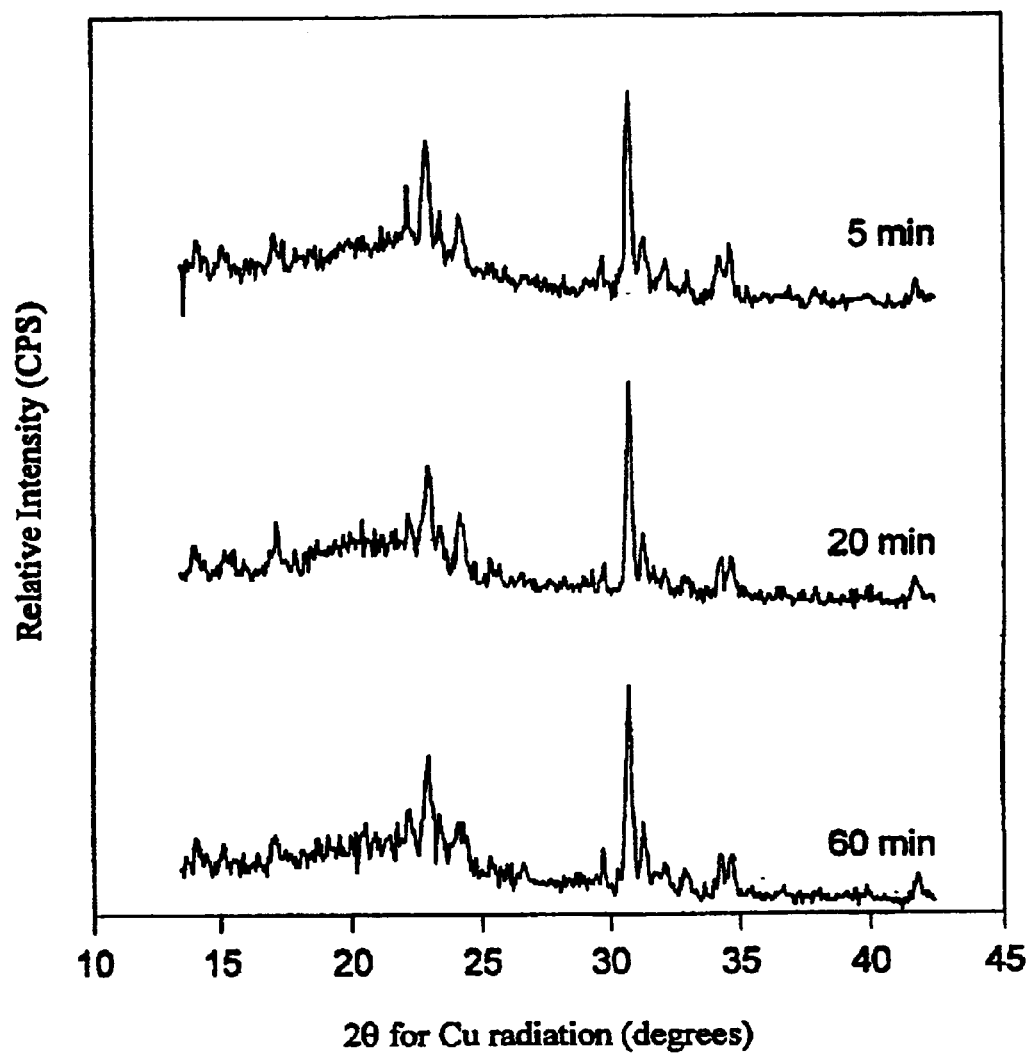
Figure 4: Glancing Angle X-Ray Diffraction Spectra illustrating the effect of sintering time on thin film phase composition.

SEM Micrograph illustrating the characteristic surface morphology of a thin film of the Ca-P colloid sintered on quartz at 1000°C.

Cross-sectional TEM of the Ca-P thin film on quartz.
Film sintered at 1000°C.

Cross-sectional TEM of the Ca-P thin film on quartz.
Unsintered film, (note underlying particle size of 5-10nm).

EDX analysis of the sintered TEM sample.

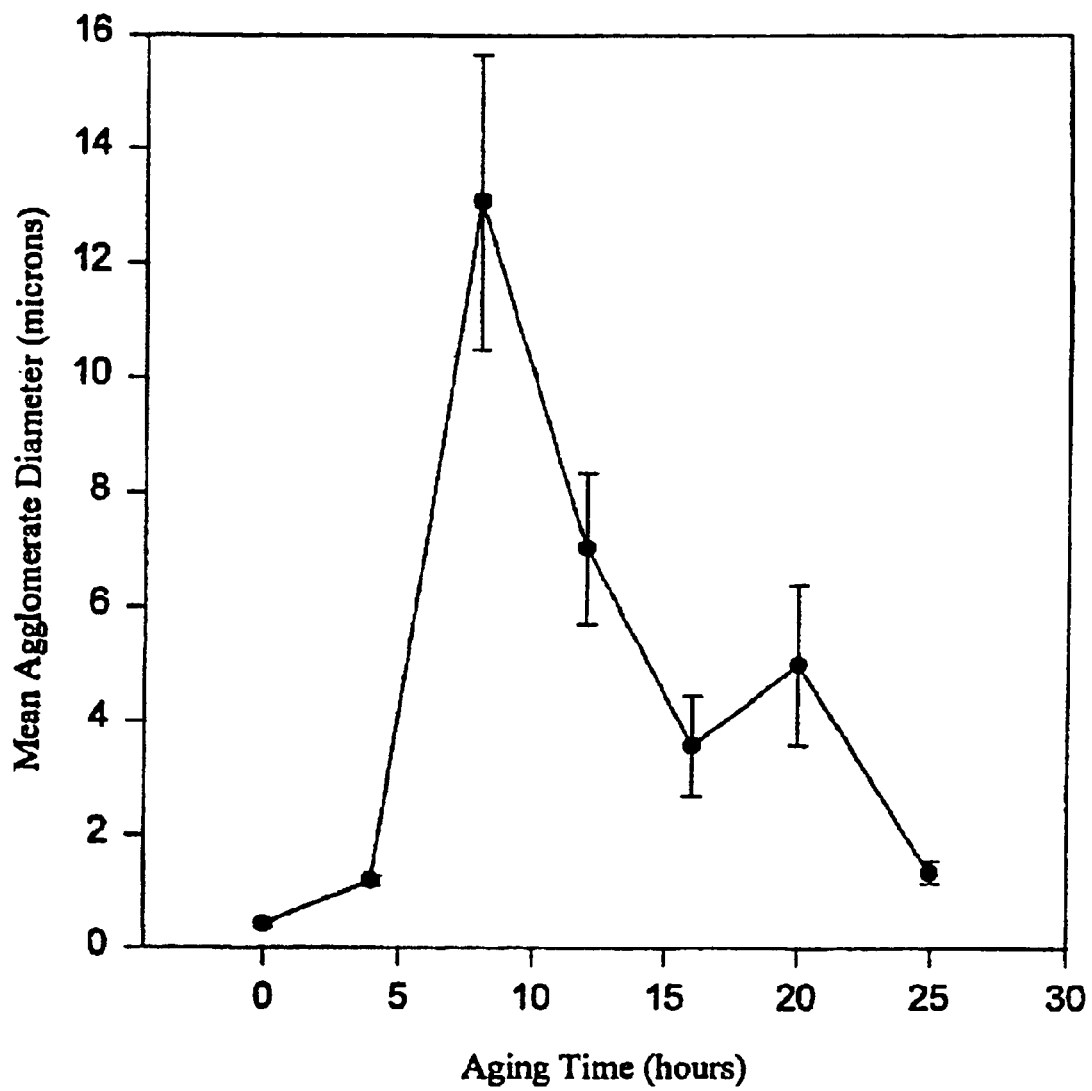
Figure 7: Average Agglomerate Size in the Ca-P colloid as a function of colloid aging period, as determined using light scattering particle analysis.

The Calculated Predominance Area Diagram Illustrating the effect of CaO activity on the relative stabilities of HA and TCP.

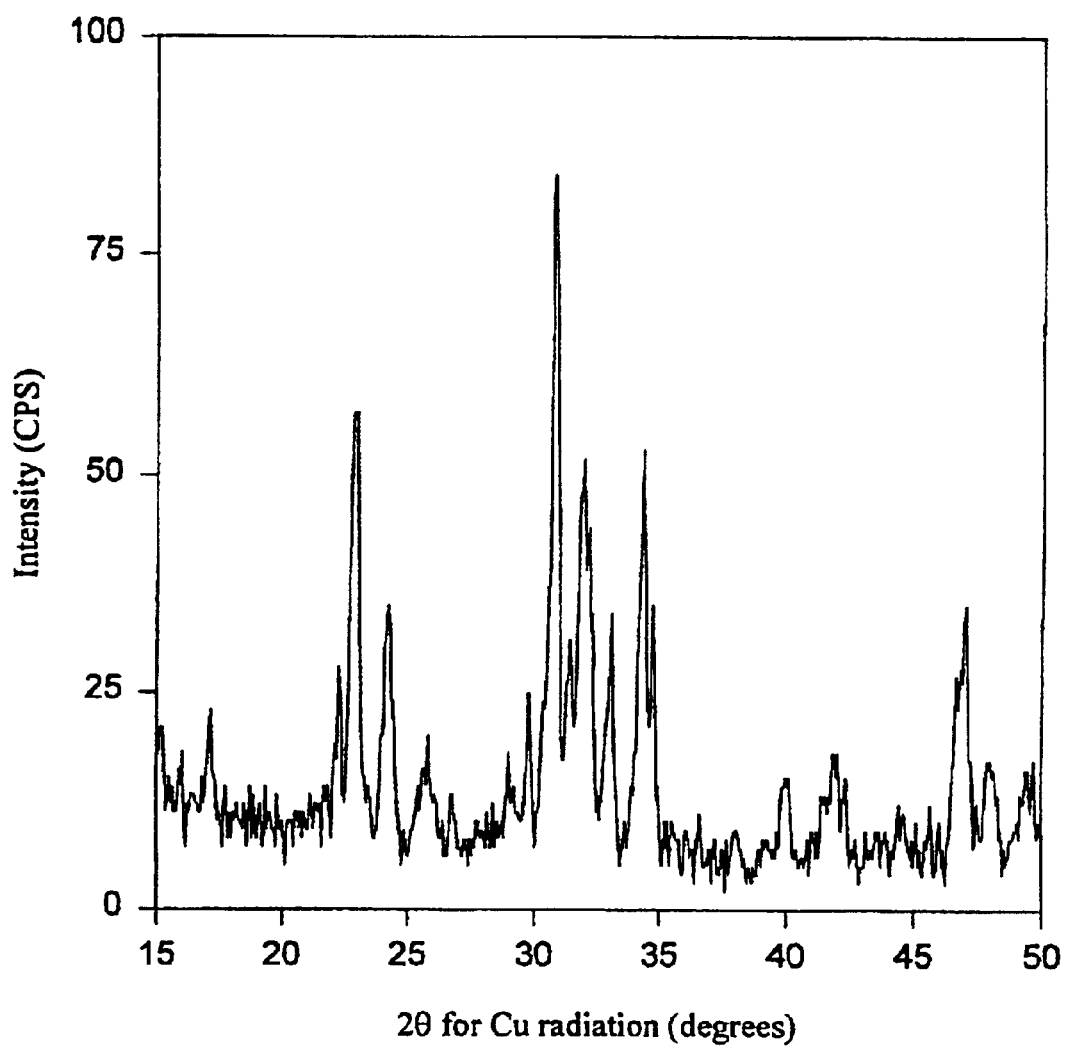
Figure 9: X-Ray Diffraction Spectrum (θ-2θ) of powder prepared from the Ca-P colloid with silicon as the introduced additive. Approximate phase ratio: 33 ± 5% HA and 67 ± 5% Si-TCP.

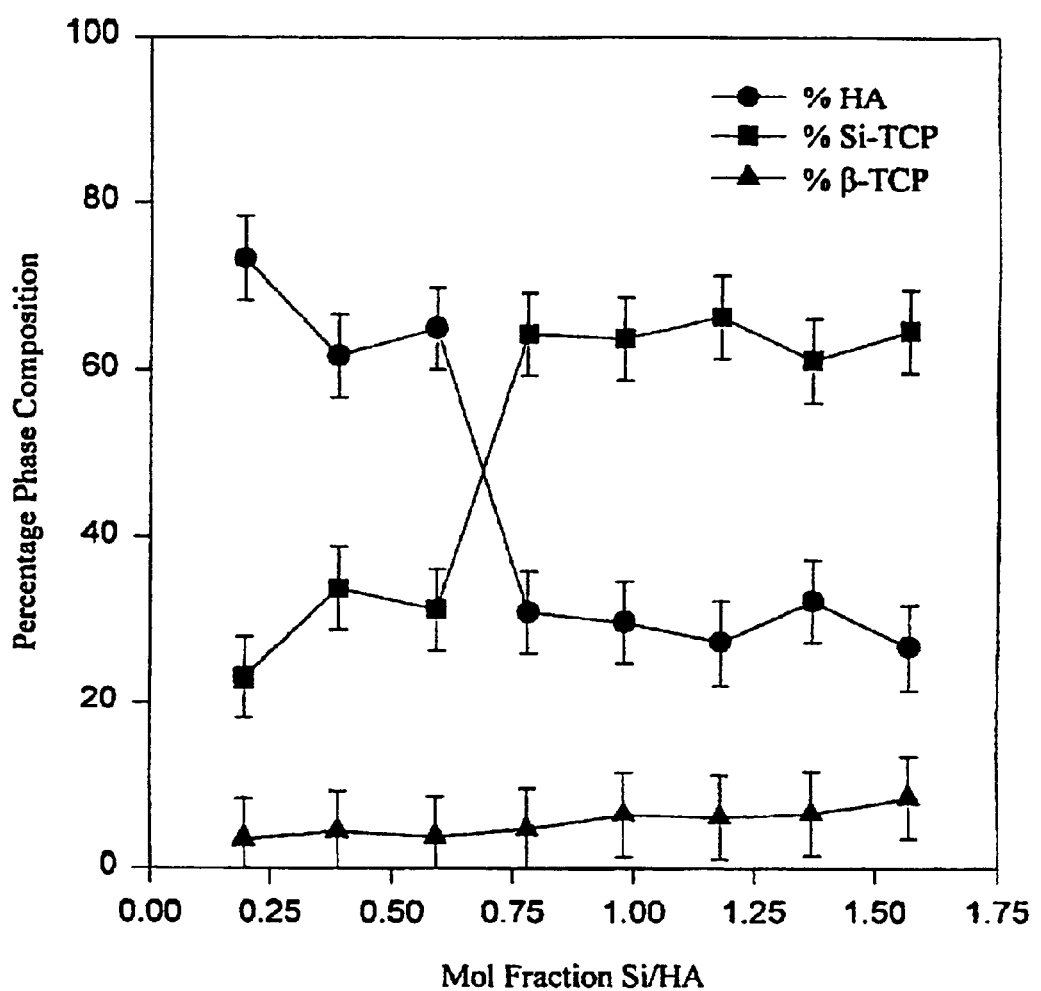
Figure 10: The Effect of Silicon Content on Phase Composition of Si-mHA powders, as determined by x-ray diffraction (θ-2θ).

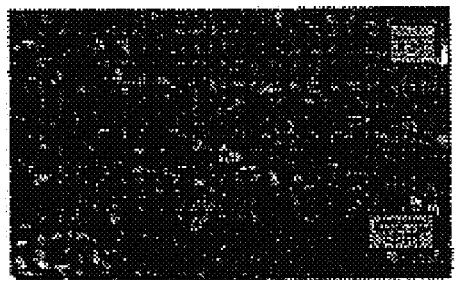

FIG. 11(a).
SEM Micrographs illustrating the characteristic surface morphology of Si-mHa ceramic pellets. Si-mHA pellets can be resorbed by the specific cellular activity of osteoclasts in a manner similar to that which occurs on natural bone.
Surface morphology Si-mHA ceramic pellet.

 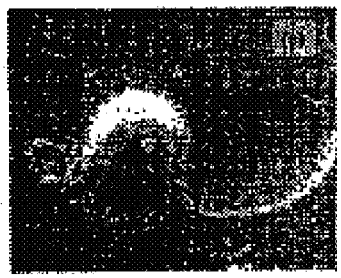

FIG. 11(b).
SEM Micrographs illustrating the characteristic surface morphology of Si-mHa ceramic pellets. Si-mHA pellets can be resorbed by the specific cellular activity of osteoclasts in a manner similar to that which occurs on natural bone.
Osteoclast lacunae on surface of Si-mHA ceramic pellet.

FIG. 11(c).
SEM Micrographs illustrating the characteristic surface morphology of Si-mHa ceramic pellets. Si-mHA pellets can be resorbed by the specific cellular activity of osteoclasts in a manner similar to that which occurs on natural bone.
Osteoclast lacunae on surface of natural bone.

Figure 12: X-Ray Diffraction Spectra (θ-2θ) of powder prepared from the Ca-P colloid with titanium as the introduced additive.
(a) Overlay of JCPDS File #9-432 (HA).
(b) Overlay of JCPDS File #9-169 (β-TCP).
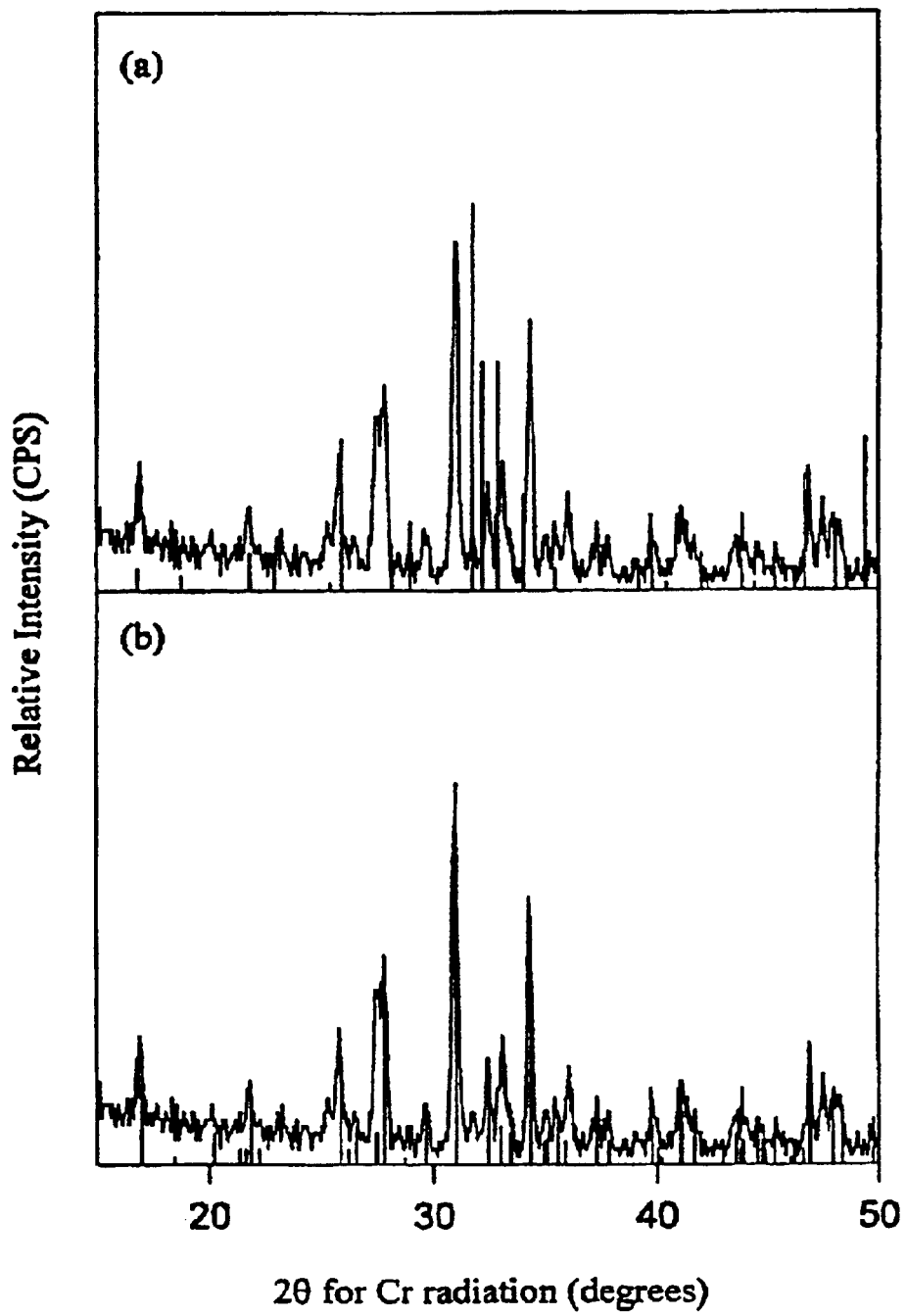

The Effect of Titanium Addition on mHA Phase Composition:
(a) no carrier (powder), (b) no carrier (ceramic pellet),
(c) 2Me (powder), (d) 2Me (ceramic pellet),
(e) ACAC (powder) and (f) ACAC (ceramic pellet).

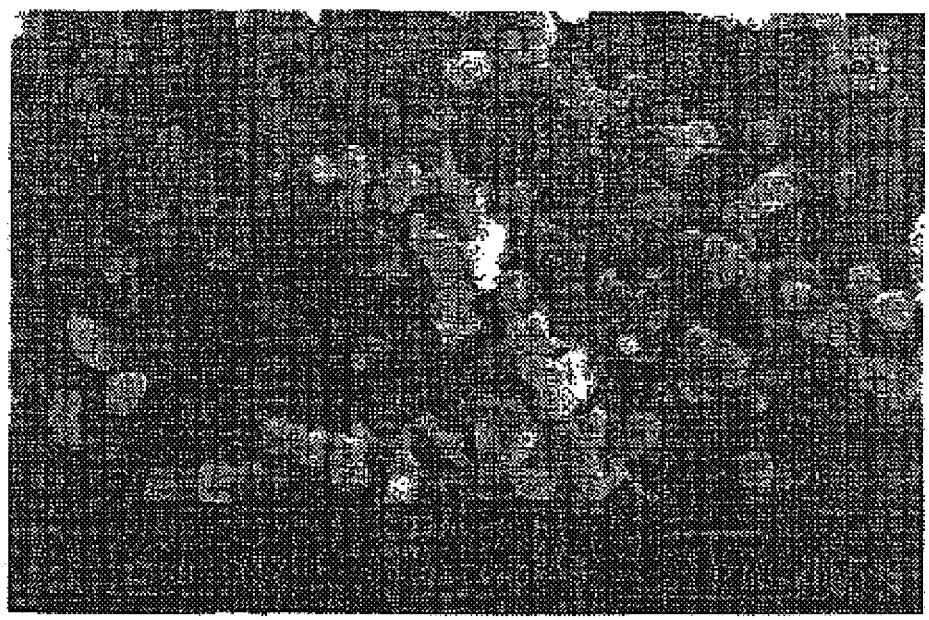

FIG. 14(a).
SEM Micrographs comparing the microstructure of Si-mHA pellets formed from the Ca-P colloid versus materials prepared from commercial sources. Si-mHA prepared using TPOS as the introduced additive.

FIG. 14(b).
SEM Micrographs comparing the microstructure of Si-mHA pellets formed from the Ca-P colloid versus materials prepared from commercial sources. cHA as a physical mixture with TPOS.

Figure 15: X-Ray Diffraction Spectra for the physical mixture of 25% $CaSiO_3$ and 75% β-TCP (sintered at 1250°C for 8 hours).
(a) Overlay of JCPDS File #9-348 (α-TCP).
(b) Overlay of JCPDS File #9-169 (β-TCP).
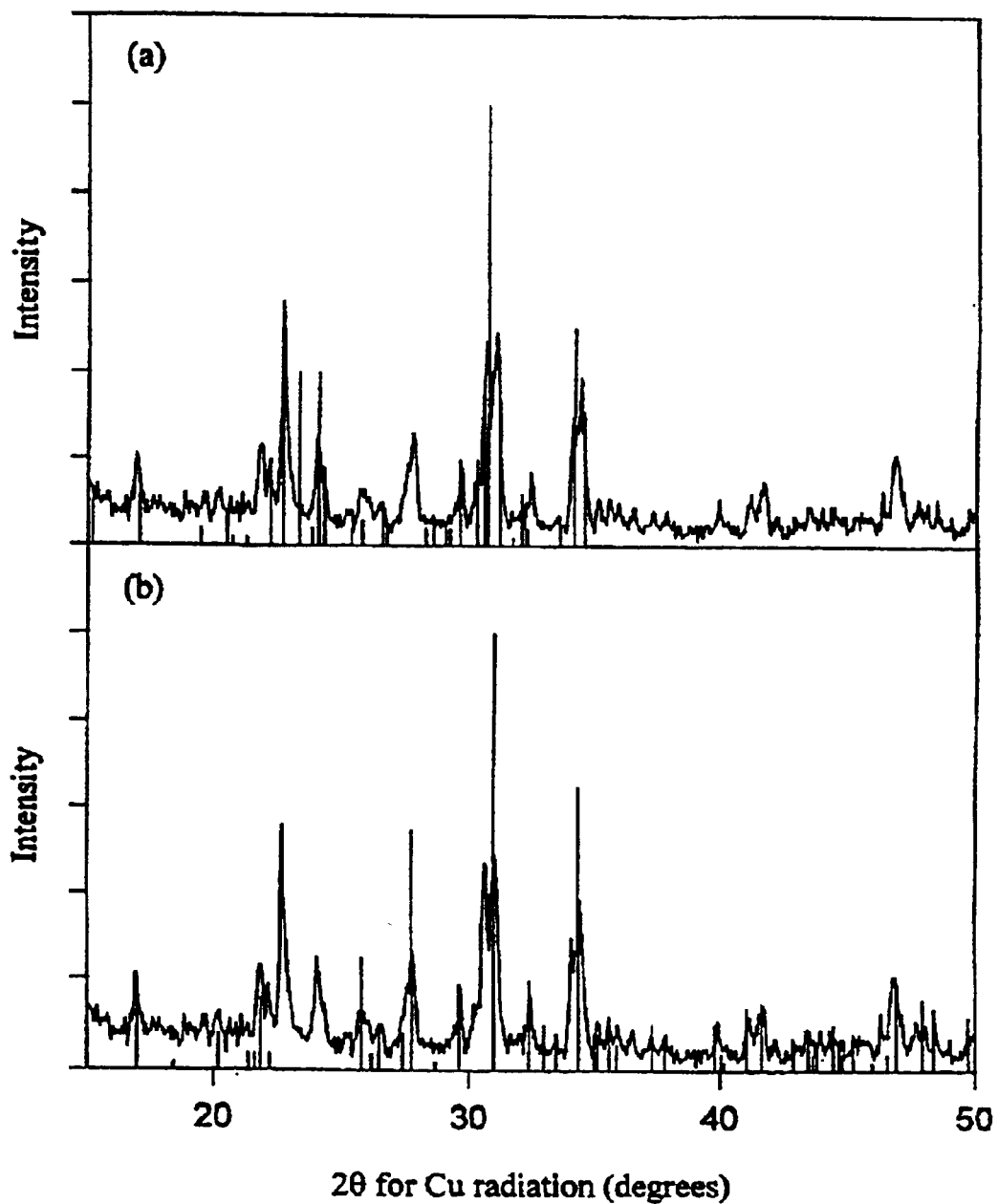

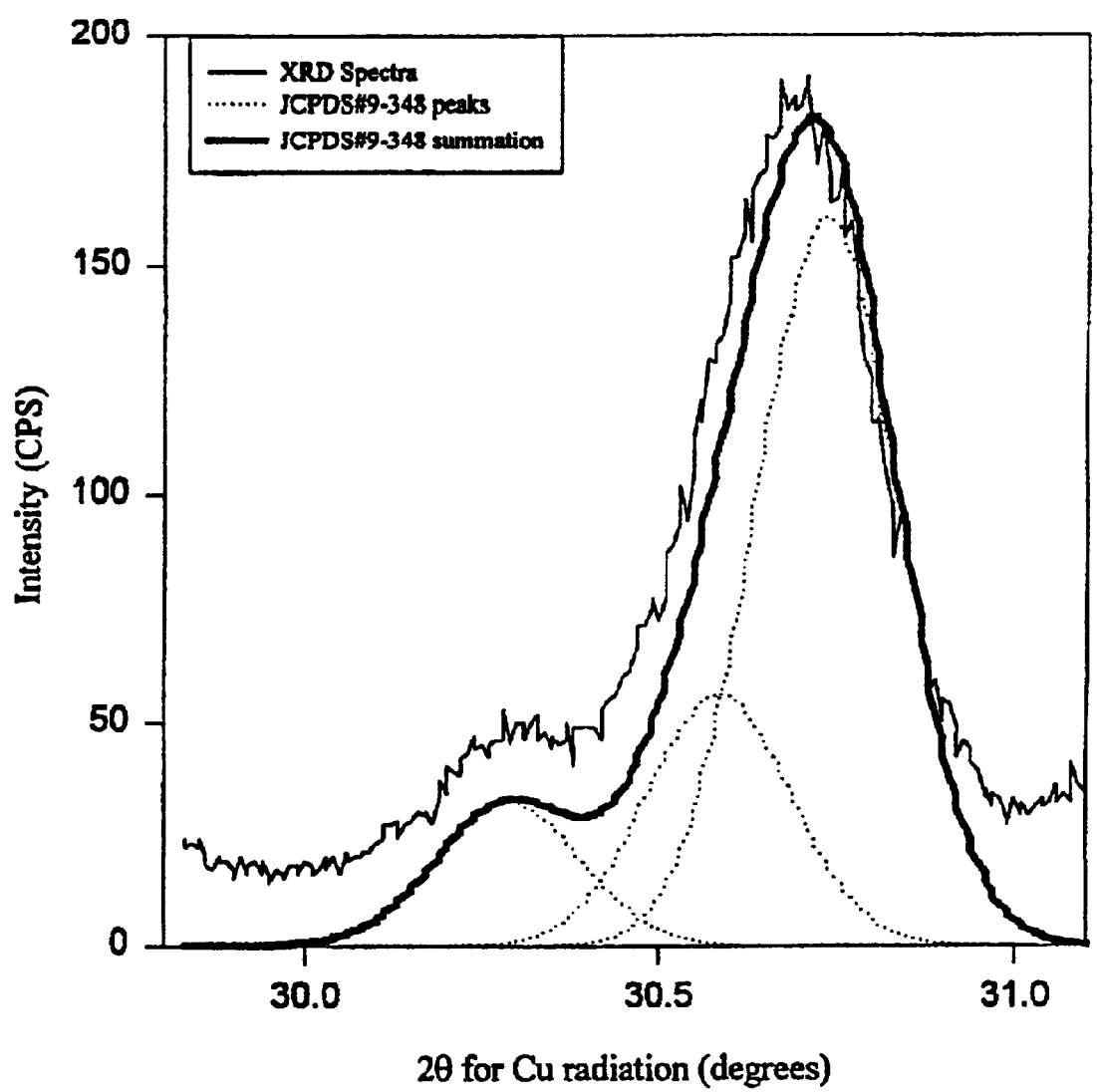
Figure 16: High Resolution X-Ray Diffraction Spectrum of Si-mHA powder. Overlay of JCPDS File #9-348 ($\alpha$-TCP) assuming a Gaussian peak shape with a peak width of 0.225°.

NMR Spectra comparing Si-mHA with comercially available reference materials. Mixture of comercial CaSiO₃ and SiO₂ powders.

NMR Spectra comparing Si-mHA with comercially available reference materials. Si-mHA powder.

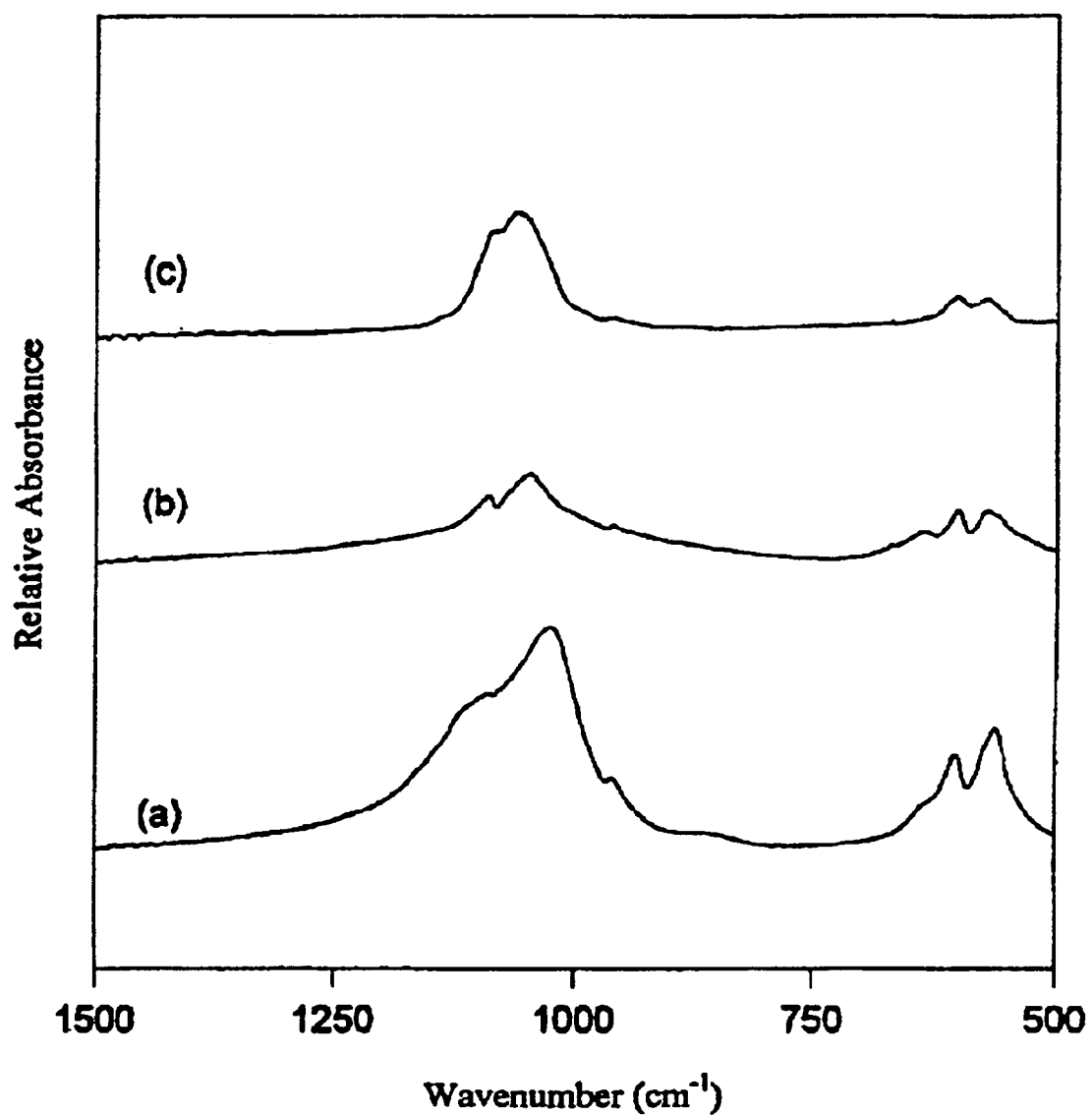
Figure 18: IR Spectra for powders sintered at 1000°C: (a) cHA, (b) mHA and (c) Si-mHA.

Figure 19: Summary of IR Spectra illustrating the effect of silicon content on the P-O stretch.
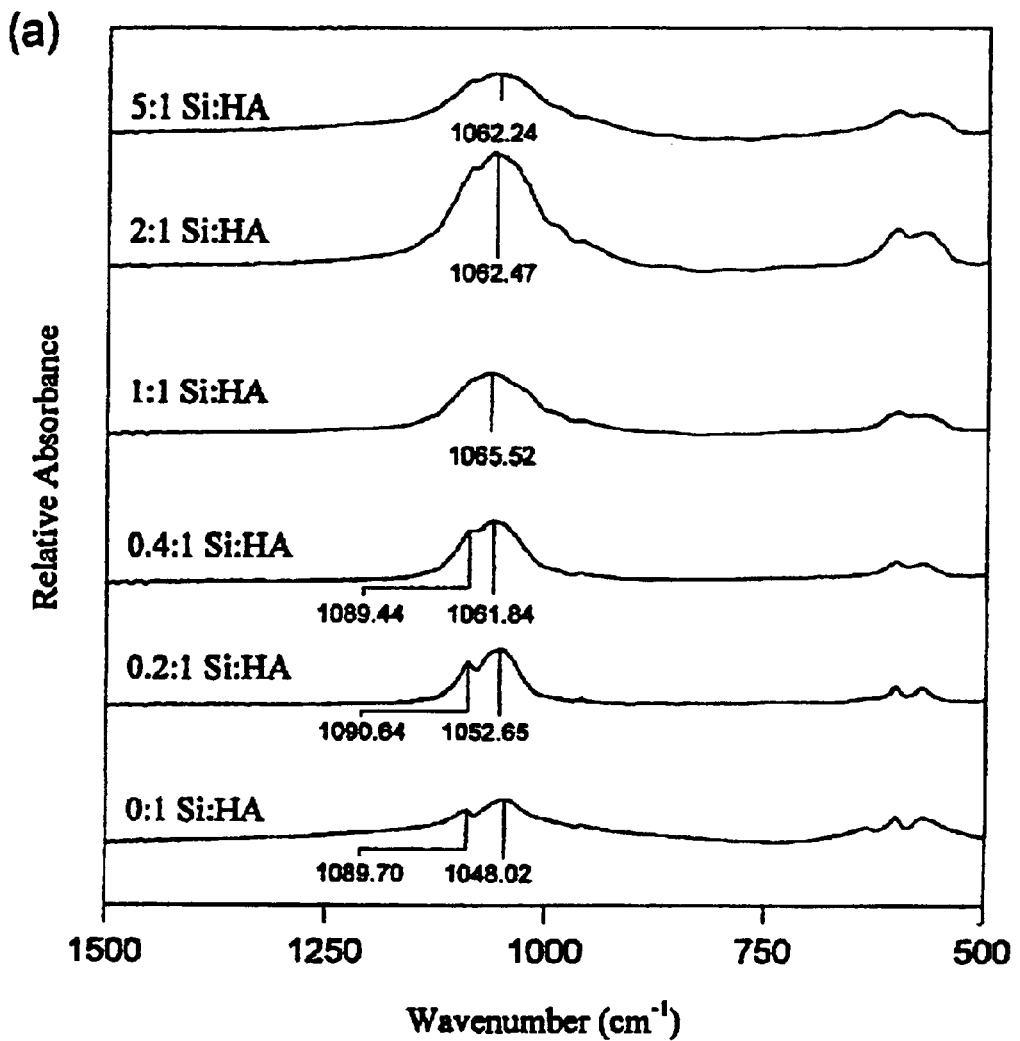
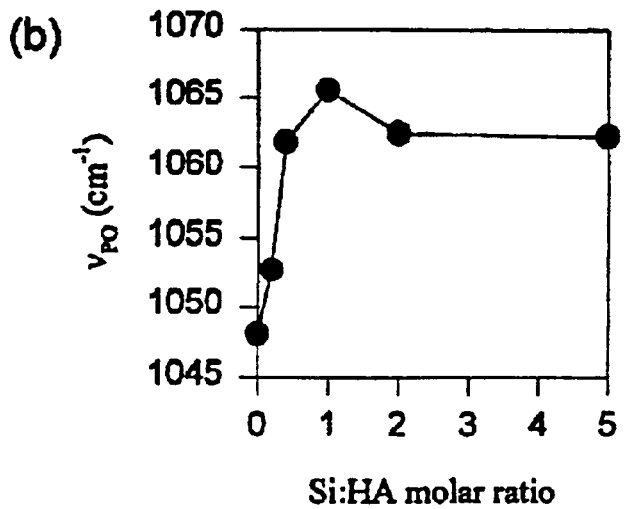

Cross-sectional SEM micrograph illustrating mineralized collagenous matrix deposited on a thin film of the stabilized composition.

Fluorescence analysis
Deposition of fluorescent mineralized matrix produced by osteoblasts cultured on the stabilized composition.

Fluorescence analysis
Control in which no osteoblasts are cultured on the stabilized composition and no fluorescent mineralized matrix is visualized.

SEM micrographs of osteoclast resorption pits on thin films of the stabilized composition.

SEM micrographs of osteoclast resorption pits on thin films of the stabilized composition.

Micro CT Image of natural bone architecture with inset SEM Micrograph of a macroporous structure formed from the Skelite™ biomaterial.

SYNTHETIC BIOMATERIAL COMPOUND OF CALCIUM PHOSPHATE PHASES PARTICULARLY ADAPTED FOR SUPPORTING BONE CELL ACTIVITY

RELATED APPLICATIONS

This application is a continuation-in-part of U.S. divisional application U.S. Ser. No. 09/971,148, filed Oct. 4, 2001, now U.S. Pat. No. 6,585,992, which is a divisional of U.S. Ser. No. 09/044,749, filed Mar. 19, 1998, issued as U.S. Pat. No. 6,323,146 which is a continuation-in-part of co-pending U.S. patent application Ser. No. 09/029,872 filed Jun. 29, 1998, which is a U.S. national phase application of PCT/CA96/00585, filed Aug. 30, 1996, which is a continuation-in-part of U.S. Ser. No. 08/576,238, filed Dec. 21, 1995, now abandoned, which claims the benefit of U.S. Provisional Application Ser. No. 60/003,157, filed Sep. 1, 1995, which are each hereby incorporated herein in their entirety by reference.

FIELD OF THE INVENTION

This invention is directed to a synthetic biomaterial compound based on stabilized calcium phosphates and more particularly to the molecular, structural and physical characterization of this compound. This compound which in the alternative may be referred to as Skelite,™ has applications in the treatment of various bone related clinical conditions such as for the repair and restoration of natural bone compromised by disease, trauma or genetic influences.

BACKGROUND OF THE INVENTION

Bone is a complex mineralizing system composed of an inorganic or mineral phase, an organic matrix phase, and water. The inorganic mineral phase is composed mainly of crystalline calcium phosphate salts while the organic matrix phase consists mostly of collagen and other noncollagenous proteins. Calcification of bone depends on the close association between the organic and inorganic phases to produce a mineralized tissue.

The process of bone growth is regulated to meet both structural and functional requirements. The cells involved in the processes of bone formation, maintenance, and resorption are osteoblasts, osteocytes, and osteoclasts. Osteoblasts synthesize the organic matrix, osteoid, of bone which after calcium phosphate crystal growth and collagen assembly becomes mineralized. Osteocytes regulate the flux of calcium and phosphate between the bone mineral and the extracellular fluid. Osteoclasts function to resorb bone and are essential in the process of bone remodeling. Disturbing the natural balance of bone formation and resorption leads to various bone disorders. Increased osteoclast activity has been demonstrated to lead to bone disease characterized by a decrease in bone density such as that seen in osteoporosis, osteitis fibrosa and in Paget's disease. All of these diseases are a result of increased bone resorption.

In order to understand the mechanisms involved which regulate bone cell function, it is important to be able to assess the normal function of bone cells and also the degree of perturbation of this activity in various bone diseases. This will lead to the identification of drugs targeted to restore abnormal bone cell activity back to within normal levels. Together with the identification of the etiology of abnormal and normal bone cell activity and the assessment of this activity, is the desire and need to develop compositions and methods for the treatment of abnormal bone cell activity, as a result of disease, surgical removal or physiological trauma all of which lead to bone tissue loss. Therapeutics which provide for the replacement and repair of bone tissue, such as with the use of bone implants, are highly desired.

Several groups have attempted to provide compositions suitable for the therapeutic replacement of bone tissue. U.S. Pat. No. 4,871,578 discloses a process for the formation of a non-porous smooth coating of hydroxyapatite suitable for implant use. U.S. Pat. No. 4,983,182 discloses a ceramic implant which comprises a sintered body of zirconia and a coating of α-TCP and zirconia, or hydroxyapatite and zirconia. U.S. Pat. No. 4,988,362 discloses a composition for the fusion of a bioceramic to another bioceramic. U.S. Pat. No. 4,990,163 discloses a coating used for the production of bioceramics which consist of α-TCP and β-TCP. Although these different compositions may be used as biocompatible coatings for implants and the like, none of these compositions have been demonstrated to participate in the natural bone remodeling process. Furthermore, none of the prior compositions developed, can be manipulated to reliably produce a range of films, thicker coatings and bulk ceramic pieces which share a common composition and morphology which leads to similar bioactive performance in vivo and in vitro.

It has therefore long been the goal of biomaterials research in the field of orthopedics to develop synthetic structures exhibiting comprehensive bioactivity. Bioactive synthetic substrates and scaffolds capable of incorporation into the natural process of bone remodeling are of interest in applications which include not only in vitro bone cell assays (Davies, J., G. Shapiro and B. Lowenberg. *Cells and Materials* 3(3) 1993; pp. 245–56), but also in vivo resorbable bone cements (Gerhart, T., R. Miller, J. Kleshinski and W. Hayes. *J Biomed Mater Res* 22 1988; pp. 1071–82 and Kurashina, K., H. Kurita, M. Hirano, J. deBlieck, C. Klein and K. deGroot. *Journal of Materials Science: Materials in Medicine* 6 1995; pp. 340–7), implantable coatings which enhance the bonding of natural bone to the implant (Tofe, A., G. Brewster and M. Bowerman. *Characterization and Performance of Calcium Phosphate Coatings for Implants* edited by E. Horowitz and J. Parr. Philadelphia: ASTM, pp. 9–15 (1994), various forms of implantable prostheses and bone repair agents (Tolman, D. and W. Laney. *Mayo Clin Proc* 68 1993; pp. 323–31 and Levitt, S., P. Crayton, E. Monroe and R. Condrate. *J Biomed Mater Res* 3 1969; pp. 683–5), and ex vivo tissue engineering (Kadiyala,S., N. Jaiswal, S. Bruder. *Tissue Engin* 3(2) 1997; pp. 173–84). The prime objective for such materials in vivo is to combine the stimulation of osteogenic activity in associated bone tissues for optimum healing, with the capability to be progressively resorbed by osteoclasts during normal continuous remodeling (Conklin, J., C. Cotell, T. Barnett and D. Hansen. *Mat Res Soc Symp Proc* 414 1996; pp. 65–70). In vitro, related functions are to provide standardized laboratory test substrates on which osteoclast resorptive function or osteoblast production of mineralized bone matrix can be assessed and quantified (Davies, J., G. Shapiro and B. Lowenberg. *Cells and Materials* 3(3) 1993; pp. 245–56). Such substrates must be stable and insoluble in the biological environment until acted upon by osteoclasts, the specific bone mineral resorbing cells.

While calcium hydroxyapatite ($Ca_5(OH)(PO_4)_3$ or HA) is the primary inorganic component of natural bone (Yamashita, K., T. Arashi, K. Kitagaki, S. Yamada and T. Umegaki. *J Am Ceram Soc* 77 1994; pp. 2401–7), trace elements are also present (*Biominerals* edited by F. Driessens and R. Verbeeck. Boston: CRC Press (1990). Calcium hydroxyapatite is but one of a number of calcium-phosphorous (Ca—P) compounds which are biocompatible. Others include octacalcium phosphate (Brown, W., M. Mathew and M. *Tung. Prog Crys Growth Charact* 4 1981; pp. 59–87) and both phases of tricalcium phosphate ($Ca_3(PO_4)_2$ or $\alpha$-TCP/$\beta$-TCP) (Elliott *J. Structure and Chemistry of the Apatites and Other Calcium Orthophosphates* New York: Elsevier (1994). Compounds, particularly HA, may show differing degrees of stoichiometry with the Ca/P ratio ranging from 1.55 to 2.2 (Meyer, J. and B. Fowler. *Inorg Chem* 21 1997; pp. 3029–35). Such materials can be artificially created by conventional high temperature ceramic processing (Santos, R. and R. Clayton. *American Mineralogist* 80 1995; pp. 336–44) or by low temperature aqueous chemistry (Brown, P., N. Hocker and S. Hoyle. *J Am Ceram Soc* 74(8) 1991; pp. 1848–54 and Brown, P. and M. Fulmer. *J Am Ceram Soc* 74(5) 1991; pp. 934–40). Most of such artificial materials show good biocompatibility in that bone cells tolerate their presence with few deleterious effects, and indeed enhanced bone deposition may occur (Ito, K., Y. Ooi. *CRC Handbook of Bioactive Ceramics* edited by T. Yamamuro, L. Hench and J. Wilson. Boca Raton, Fla.: CRC Press, pp. 39–51 (1990) and Ohgushi, H., M. Okumura, S. Tamai, E. Shors and A. Caplan. *J Biomed Mater Res* 24 1990; pp. 1563–70). Currently, the most recognized medical application of calcium phosphates is the coating of implantable prosthetic devices and components by thermal or plasma spray to render the surface osteoconductive. It has been noted that Ca—P ceramics which are stable in biological environments are often a mixture of individual compounds (LeGeros, R., G. Daculsi. *CRC Handbook of Bioactive Ceramics* edited by T. Yamamuro, L. Hench and J. Wilson. Boca Raton: CRC Press, (1990)). However, despite the osteogenic potential of these artificial materials, none actively participate in the full process of natural bone remodeling.

In an effort to understand the cellular mechanisms involved in the remodeling process, several research groups have attempted to develop methods to directly observe the activity of isolated osteoclasts in vitro. Osteoclasts, isolated from bone marrow cell populations, have been cultured on thin slices of natural materials such as sperm whale dentine (Boyde et al Brit. Dent. J. 156, 216, 1984) or bone (Chambers et al J. Cell Sci. 66, 383, 1984). The latter group have been able to show that this resorptive activity is not possessed by other cells of the mononuclear phagocyte series (Chambers & Horton, Calcif Tissue Int. 36, 556, 1984). More recent attempts to use other cell culture techniques to study osteoclast lineage have still had to rely on the use of cortical bone slices (Amano et al. and Kerby et al J. Bone & Min. Res. 7(3)) for which the quantitation of resorptive activity relies upon either two dimensional analysis of resorption pit areas of variable depth or stereo mapping of the resorption volume. Such techniques provide at best an accuracy of approximately 50% when assessing resorption of relatively thick substrata. In addition these analysis techniques are also very time consuming and require highly specialized equipment and training. Furthermore, the preparation and subsequent examination of bone or dentine slices is neither an easy nor practical method for the assessment of osteoclast activity.

The use of artificial calcium phosphate preparations as substrata for osteoclast cultures has also met with little success. Jones et al (Anat. Embryol 170, 247, 1984) reported that osteoclasts resorb synthetic apatites in vitro but failed to provide experimental evidence to support this observation. Shimizu et al (Bone and Mineral 6, 261, 1989) have reported that isolated osteoclasts resorb only devitalized bone surfaces and not synthetic calcium hydroxyapatite. These results would indicate that functional osteoclasts are difficult to culture in vitro.

In the applicant's published international PCT application WO94/26872, cell-mediated resorption was shown to occur on a calcium phosphate-based thin film formed by the high temperature processing of a calcium phosphate colloidal suspension on quartz substrates. When used in vitro, these ceramic films exhibited multiple discrete resorption events (lacunae) across their surface as a result of osteoclast activity, with no evidence of dissolution arising from the culture medium. The regular margins of these lacunae correspond closely to the size and shape of the ruffled borders normally produced by osteoclasts as the means by which they maintain the localized low pH required to naturally resorb bone mineral in vivo. Enhanced deposition of mineralized bone matrix also occurs on these ceramics in the presence of osteoblasts.

It is now demonstrated by the Applicant's that these thin film ceramics exhibit two general characteristics: (1) the presence of a mixture of Ca—P containing phases comprising approximately 33% HA and approximately 67% of a silicon stabilized calcium phosphate and (2) a unique morphology. Importantly, it was noted that the thermal processing of the Ca—P colloid at 1000° C. resulted in an HA powder, while the same colloidal suspension processed on quartz had a mixed HA and silicon stabilized calcium phosphate phase composition. Energy dispersive X-ray analysis of the film demonstrated the presence of Si in the coating while cross-sectional transmission electron microscopy indicated a microporous physical structure.

Applicants have discovered that the presence of stabilizing entities can stabilize the composition and prevent its degradation in physiological fluids. Hence, disappearance of calcium phosphate entities from a film, coating or bulk ceramic piece of this composition, is substantially due to the activity of the osteoclasts and not due to a dissolution process. The stabilized artificial bioactive composition is the first such composition which supports both osteoclast and osteoblast activity and which allows for the reliable assessment of the physiological activities of both cell types as well as for the development of both diagnostic and therapeutic strategies.

In view of the clinical importance of developing a synthetic bone graft that is both osteogenic and can participate in the body's natural cell-based remodeling process, it was important to focus on the role of introduced additives such as silicon in the formation of a calcium phosphate-based biomaterial compound capable of being assimilated and remodeled into natural bone with the aid of the activity of osteoclasts and osteoblasts. Since the compound could only be characterized by the preparation method, it was crucial to be able to both physically and chemically characterize the compound. In particular, it was important to characterize the physical structure of the compound and more importantly, the specific molecular and chemical structure of the stabilized compound in order to be able to understand why the new compound worked so well in biological conditions affecting the skeleton. The physical, molecular and chemical characterization of the compound could also provide for the development of further uses of the compound in the treatment of several different types of bone-related clinical conditions. In addition, this would also allow further chemical alteration of the compound in order that it could be designed for use in specific in vivo, in vitro and ex vivo applications.

The Applicant's work now pointed to the transformation of HA into a stabilized calcium phosphate phase. Surprisingly, during the difficult course of explicit characterization of the compound from a molecular standpoint, it was found-that the resultant stabilized compound was an entirely new compound herein described and termed Skelite™.

SUMMARY OF THE INVENTION

The present invention provides a stabilized composition comprising a synthetic biomaterial compound which allows for a wide variety of diagnostic and therapeutic applications. The biomaterial compound, in accordance with an aspect of the invention, can be used to provide a range of fine or coarse powders, pellets, three-dimensional shaped pieces, thin films and coatings which share a common globular morphology and an interconnected microporosity. In addition, the biomaterial compound can be formed as a macroporous structure in order to provide an artificial three dimensional geometry similar to that found in bone in vivo. The biomaterial compound, made in any form, encourages the activity of bone cells cultured thereon and also allows for the development of ex vivo engineered artificial bone tissues for use as bone grafts.

The created stabilized calcium phosphate compound has only now been specifically characterized with respect to its physical and chemical structure leading to the realization that the stabilized compound was an entirely new compound never before described. The biomaterial compound is made by the high temperature processing of a fine precipitate, formed from a colloidal suspension and stabilized using an additive with an appropriate sized ionic radius that enables substitution into the Ca—P lattice. The compound typically coexists with calcium hydroxyapatite and is itself a novel stabilized calcium phosphate compound having a microporous morphology based on inter-connected particles of about 0.2–1.0 $\mu$m in diameter. The compound is essentially insoluble in biological media but is resorbable when acted upon by osteoclasts. It also promotes organic bone matrix deposition by osteoblasts and can be assimilated into natural bone during the natural course of bone remodeling through the activity of osteoclasts and osteoblasts. The compound has been extensively analyzed using X-ray diffraction, infrared spectroscopy, nuclear magnetic resonance spectroscopy, and light scattering particle analysis. Results now indicate that the characteristic features of the compound arise during sintering through substitution reactions where a stabilizing element such as silicon enters the calcium phosphate lattice under conditions of high chemical reactivity. The crystallographic features are linked through the glaserite form of the apatite structure.

According to an aspect of the present invention a biomaterial compound is provided comprising calcium, oxygen and phosphorous, wherein at least one of the elements is substituted with an element having an ionic radius of approximately 0.1 to 1.1 Å.

According to another aspect of the present invention is a biomaterial compound having the formula $(Ca_{1-w}A_w)_i[(P_{1-x-y-z}B_xC_yD_z)O_j]_2$; wherein A is selected from those elements having an ionic radius of approximately 0.4 to 1.1 Å; B, C and D are selected from those elements having an ionic radius of approximately 0.1 to 0.4 Å; w is greater than or equal to zero but less than 1; x is greater than or equal to zero but less than 1; y is greater than or equal to zero but less than 1; z is greater than or equal to zero but less than 1; x+y+z is greater than zero but less than 1; i is greater than or equal to 2 but less than or equal to 4; and j equals 4-$\delta$, where $\delta$ is greater than or equal to zero but less than or equal to 1.

Specific compounds of the present invention include but are not limited to $Ca_3(P_{0.750}Si_{0.25}O_{3.875})_2$ and $Ca_3(P_{0.9375}Si_{0.0625}O_{3.96875})_2$.

The knowledge of the specific molecular and chemical properties of the compound of the present invention allows for the development of several uses of the compound in various bone-related clinical conditions. Such applications may include orthopedic, maxillo-facial and dental applications where the compound can be fabricated to exist as a fine or coarse powder, pellets, three-dimensional shaped pieces, macroporous structures, thin films and coatings.

According to yet another aspect of the present invention is a method for substituting natural bone at sites of skeletal surgery in human and animal hosts with a biomaterial compound comprising calcium, oxygen and phosphorous wherein at least one of the elements is substituted with an element having an ionic radius of approximately 0.1 to 1.1 Å. The method comprises the steps of implanting the biomaterial compound at the site of skeletal surgery wherein such implantation promotes the formation of new bone tissue at the interfaces between the biomaterial compound and the host, the progressive removal of the biomaterial compound primarily through osteoclast activity, and the replacement of that portion of the biomaterial compound removed by further formation of new bone tissue by osteoblast activity, such progressive removal and replacement being inherent in the natural bone remodeling process.

In accordance with another aspect of the present invention is a method for repairing large segmental skeletal gaps and non-union fractures arising from trauma or surgery in human and animal hosts using a biomaterial compound comprising calcium, oxygen and phosphorous wherein at least one of the elements is substituted with an element having an ionic radius of approximately 0.1 to 1.1 Å. The method comprises the steps of implanting the biomaterial compound at the site of the segmental skeletal gap or non-union fracture wherein such implantation promotes the formation of new bone tissue at the interfaces between the biomaterial compound and the host, the progressive removal of the biomaterial compound primarily through osteoclast activity, and the replacement of that portion of the biomaterial compound removed by further formation of new bone tissue by osteoblast activity, such progressive removal and replacement being inherent in the natural bone remodeling process.

According to yet another aspect of the present invention is a method for aiding the attachment of implantable prostheses to skeletal sites and for maintaining the long term stability of the prostheses in human and animal hosts using a biomaterial compound comprising calcium, oxygen and phosphorous wherein at least one of the elements is substituted with an element having an ionic radius of approximately 0.1 to 1.1 Å. The method comprises the steps of coating selected regions of an implantable prosthesis with the biomaterial compound, implanting the coated prosthesis into a skeletal site wherein such implantation promotes the formation of new bone tissue at the interfaces between the biomaterial compound and the host, the generation of a secure interfacial bond between the host bone and the coating, the subsequent progressive removal of the coating primarily through osteoclast activity such that the coating is diminished, and the replacement of that portion of the biomaterial compound removed by further formation of new bone tissue to generate a secure interfacial bond directly between the host bone and the prosthesis.

According to yet another aspect of the present invention is a method for providing tissue-engineering scaffolds for bone replacement in human or animal hosts using a biomaterial compound comprising calcium, oxygen and phosphorous wherein at least one of the elements is substituted with an element having an ionic radius of approximately 0.1 to 1.1 Å. The method comprises the steps of forming the biomaterial compound as a macroporous structure comprising an open cell construction with interconnected voids, combining mature and/or precursor bone cells with the macroporous structure, and allowing the cells to infiltrate the structure in order to develop new mineralized matrix throughout the structure.

The knowledge of the structure of the novel compound of the present invention also allows for the use of the compound as a carrier for various pharmaceutical agents including but not restricted to bone growth factors and other agents affecting bone growth and remodeling.

According to another aspect of the present invention is a method for delivering pharmaceutical agents to the site of skeletal surgery in human or animal hosts using a biomaterial compound comprising calcium, oxygen and phosphorous wherein at least one of said elements is substituted with an element having an ionic radius of approximately 0.1 to 1.1 Å. The method comprises combining a pharmaceutical agent with the biomaterial compound and applying the pharmaceutical agent combined with the biomaterial compound to a site of skeletal surgery, wherein such application results in controlled local release of the pharmaceutical agent.

The biomaterial compound may be combined with additives such as those which increase the mechanical strength and toughness of the compound in order to provide additional functions for specific applications. The biomaterial compound may also be combined with various calcium materials such as calcium hydroxyapatite, α-TCP, β-TCP, octocalcium phosphate, tetracalcium phosphate, dicalcium phosphate and calcium oxide either as a physical mixture or as a solid solution.

The biomaterial compound has a distinguishable microporous and nanoporous structure along with a crystallography that is similar yet different from that of α-TCP. The new compound exhibits monoclinic pseudo-rhombic symmetry and is in the monoclinic space group $P2_1/a$. Furthermore, the new compound has a portion of the phosphorous substituted by an element having a suitable ionic radius.

The knowledge of the chemical formula of the biomaterial compound and the mechanism behind its bioactivity and stability in biological environments allows for the use of this compound in vivo for the treatment of various bone related clinical conditions. In particular, the compound may be used to help repair and restore natural bone that has been compromised by disease, trauma, or genetic influences.

In accordance with yet a further aspect of the invention is a bioactive synthetic sintered composition for providing a morphology capable of consistently supporting bone cell activity thereon, the composition comprising stabilized calcium phosphate compound developed by the conversion of a hydroxyapatite substance in the presence of stabilizing entities at sintering temperatures wherein the stabilizing entities stabilize and insolubilize the calcium phosphate compound.

In accordance with a further aspect of the present invention is a process for preparing a synthetic sintered composition comprising a stabilized calcium phosphate compound having a morphology suitable for supporting bone cell activity thereon, the process comprising converting a hydroxyapatite substance in the presence of stabilizing entities at sintering temperatures wherein the stabilizing entities stabilize and insolubilize the calcium phosphate compound.

According to yet a further aspect of the present invention is a synthetic sintered microporous polycrystalline structure for supporting bone cell activity, the structure comprising a stabilized calcium phosphate compound having a globular morphology of interconnected rounded particles with an interconnected microporosity in said structure.

In accordance with yet a further aspect of the present invention is an implant comprising: a) a scaffold for supporting the implant; and b) a layer of a stabilized calcium phosphate compound developed by the conversion of a hydroxyapatite substance in the presence of stabilizing entities at sintering temperatures wherein the stabilizing entities insolubilize and stabilize the calcium phosphate compound.

In accordance with another aspect of the present invention is an implant comprising: a) a scaffold for supporting the implant; b) a layer of a stabilized calcium phosphate compound developed by the conversion of a hydroxyapatite substance in the presence of stabilizing entities at sintering temperatures wherein the stabilizing entities insolubilize and stabilize the calcium phosphate compound; c) a boundary layer deposited by osteoblasts cultured on the layer of the stabilized calcium phosphate compound; and d) a mineralized collagenous matrix secreted by such cultured osteoblasts.

According to another aspect of the present invention is a method for the culturing of functional bone cells, the method comprising applying a suspension of bone cells in physiological media to a synthetic sintered film comprising a stabilized calcium phosphate compound on a substrate; and incubating the bone cells for a period of time to allow expression of bone cell biological activity.

According to a further aspect of the present invention is a kit for monitoring and quantifying the activity of bone cells, the kit comprising a substrate having a sintered film of a stabilized calcium phosphate compound and a multiwell bone cell culture device adhered to the substrate.

In accordance with another aspect of the present invention is a method for the production of a calcium phosphate biomaterial powder, the method comprising:

(a) mixing a silica colloid with a calcium phosphate colloidal suspension;
(b) spray drying (a) into powder;
(c) sintering said powder.

In an aspect of the invention, the silica colloid is a finely divided fumed silica colloid.

In accordance with yet another aspect of the present invention is a method for the production of a calcium phosphate biomaterial powder, the method comprising:

(a) mixing a solution of calcium nitrate tetrahydrate with ammonium dihydrogen orthophosphate to produce a calcium phosphate colloidal suspension;
(b) mixing (a) with a finely divided fumed silica colloid;
(c) spray drying (b) into a powder; and
(d) sintering using a heating profile with a ramp rate of about 5° C. per minute, drying at about 200° C. for about 180 minutes, calcining at about 550° C. for about 60 minutes and sintering at about 1000° C. for about 60 minutes.

The silica colloid may be added at any time in the process and preferably, prior to the aging and centrifugation of the calcium phosphate colloidal suspension.

According to another aspect of the invention is a powdered calcium phosphate biomaterial made by the method recited herein and containing up to about 10 weight percent of silicon.

BRIEF DESCRIPTION OF THE DRAWINGS

The present invention will be further understood from the following description with reference to the Figures, in which:

FIG. 1 shows a X-Ray Diffraction Spectrum (θ-2θ) of powder prepared from the Ca—P colloid with no introduced additives and sintered at 1000° C.

FIG. 2 shows glancing angle XRD spectra of a thin film of the Ca—P colloid sintered on quartz at 1000° C.

FIG. 3 shows GA-XRD spectra illustrating the effect of sintering temperature on thin film phase composition;

FIG. 4 shows GA-XRD spectra illustrating the effect of sintering time on thin film phase composition;

FIG. 7 shows the average agglomerate size in the Ca—P colloid as a function of colloid aging period, as determined using light scattering particle analysis;

FIG. 9 shows a θ2θ XRD spectrum of powder prepared from the Ca—P colloid with silicon as the introduced additive. Approximate phase ratio: 33±5% HA and 67±5% Si-TCP;

FIG. 10 shows the effect of silicon content on phase composition of Si-mHA powders, as determined by x-ray diffraction (θ-2θ);

FIG. 11 shows SEM micrographs illustrating the characteristic surface morphology of Si-mHA ceramic pellets. Si-mHA pellets can be resorbed by the specific cellular activity of osteoclasts in a manner similar to that which occurs on natural bone. (a) Surface morphology Si-mHA ceramic pellet; (b) Osteoclast lacunae on surface of Si-mHA ceramic pellet; and 11(c) Osteoclast lacunae on surface of natural bone;

FIG. 12 shows θ-2θ XRD spectra of powder prepared from the Ca—P colloid with titanium as the introduced additive.

FIG. 14 shows SEM micrographs comparing the microstructure of Si-mHA pellets formed from the Ca—P colloid versus materials prepared from commercial sources. (a) Si-mHA prepared using TPOS as the introduced additive; and (b) cHA as a physical mixture with TPOS.

FIG. 15 shows the XRD spectra for the physical mixture of 25% $CaSiO_3$ and 75% α-TCP sintered at 1250° C. for 8 hours;

FIG. 16 shows a high resolution XRD spectrum of Si-mHA powder;

FIG. 18 shows IR spectra for powders sintered at 1000° C.: (a) cHA, (b) mHA and (c) Si-mHA; and FIG. 19 shows a summary of the IR spectra illustrating the effect of silicon content on the P—O stretch.

Figure 5:
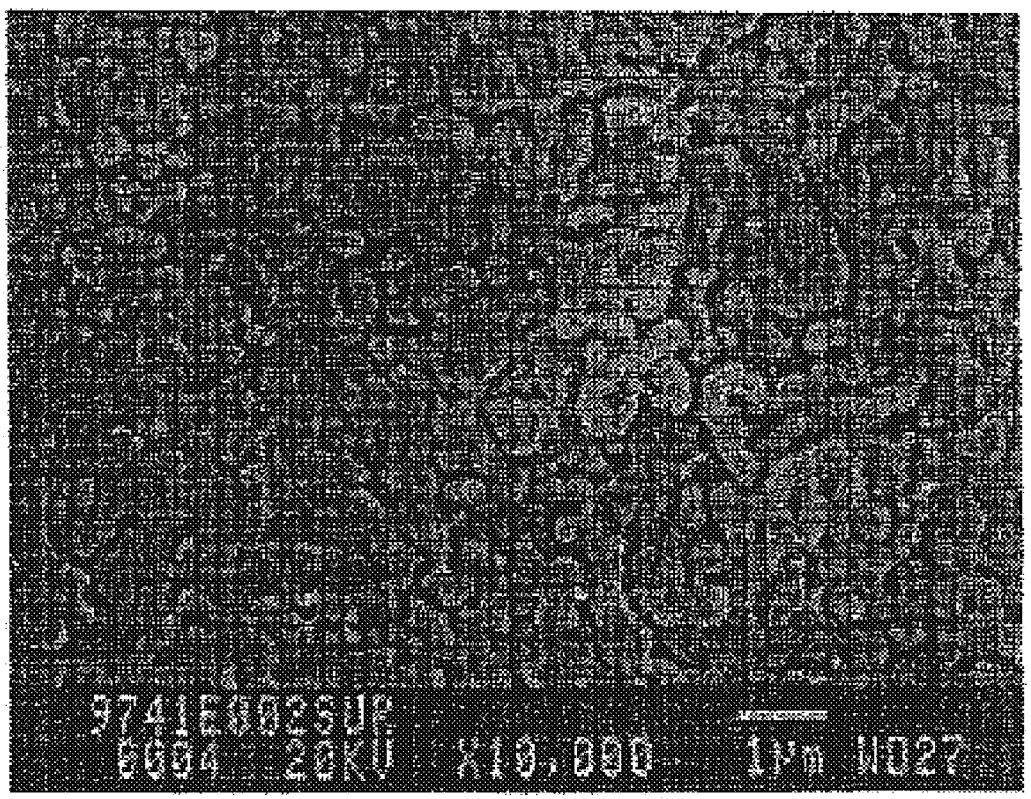
FIG. 5 shows a SEM micrograph illustrating the characteristic surface morphology of a thin film of the Ca—P colloid sintered on quartz at 1000° C.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENTS

The Applicants have developed a process to provide a stabilized calcium phosphate synthetic biomaterial compound which is fully biocompatible and has a morphology capable of consistently supporting bone cell activity thereon. This is provided in accordance with that method described in the Applicant's co-pending published PCT application WO 94/26872, the subject matter of which is incorporated herein by reference. The preferred embodiment for making the compound of the present invention is described herein in the accompanying examples.

The compound of the present invention is herein referred to as a biomaterial compound due to its bioactive nature in both in vitro and in vivo systems. Bioactivity refers to the ability of the biomaterial compound to support osteoclast and osteoblast activity and the ability to be assimilated with natural bone by the activity of these cells. Although the compound was characterized with respect to the process by which it is made, both the physical and molecular structure were unknown and could not be determined. It was however essential to characterize the compound further with respect to its physical and chemical structure so as to better understand the properties of the compound as well as to understand why the compound was so well adapted for osteoclast and osteoblast activity. The knowledge of the chemical structure of the compound also allows for the modification of the compound for therapeutic use in the treatment of certain clinical conditions.

Early data pointed to the fact that that the compound was silicon stabilized. With further difficult and tedious analysis it was surprisingly found that the compound was in fact a completely new synthetic stabilized calcium phosphate compound never before characterized and herein referred to as Skelite™. Where silicon is used as the introduced additive to form Skelite™ the compound is referred to as Si-TCP.

One reason for the great difficulty in establishing the chemical formula for the new compound was due to the complex and large structure of Ca—P compounds such as HA as well as the changing phase transitions that occurred during the sintering process. The chemical identification of this compound was only realized and developed after lengthy analysis of various Ca—P powders, thin films and pellets prepared with introduced additives. Standard XRD analysis was performed on samples prepared by a variety of compositional and thermal processing routes. Results were initially considered to be consistent with the conclusion that the materials were a mixture of α-TCP and HA, and that the calcium silicates predicted by the FACT database (Bale, C. W., A. D. Pelton, and W. T. Thompson. *FACT Database* [computer program]. Contact: W. T. Thompson, Chemical and Materials Engineering, Royal Military College, Kingston, Canada, K7K 5L0 (1997) existed as a glassy phase at the grain boundaries. Since no JCPDS file was available for Skelite™ and the peak positions were indicative of α-TCP using standard XRD techniques, the identification of Skelite™ was unforeseen. Furthermore, one would not expect to find that substitution is taking place at such low temperatures. A complex and unobvious combination of analysis techniques had to be performed to successfully identify and characterize the new compound. These studies, described as follows led to the characterization of the new compound, an additive stabilized calcium phosphate compound, Skelite™.

For clarity, several materials referred to herein are defined as follows. For the commercially available materials cHA refers to commercial calcium hydroxyapatite (HA), calcium silicate refers to $CaSiO_3$ and silica refers to $SiO_2$. For the internally prepared materials mHA refers to microporous calcium hydroxyapatite (HA), Si-mHA refers to Si-TCP plus mHA. These materials are further defined in Table 1.

Analysis of Pure (No Introduced Additives) mHA Powders

Using reaction (1) and analogous reactions, a fine colloidal precipitate of HA in ammoniated water can be achieved under conditions where the pH is greater than 10.

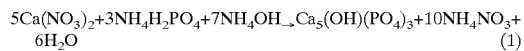

(1)

FIG. 1 shows that powders prepared from the colloidal suspension of equation (1) with no introduced additives and sintered at 1000° C. are HA (JCPDS File #9-432). The particle size of sintered powders, after mild grinding following sintering, is about 1 μm as determined by SEM.

Analysis of Thin Films on Quartz Substrates

FIG. 2 shows that the film on quartz has a crystallographic structure which was more complex than that for a powder sintered under the same conditions. The structure consists of two major phases, HA and Si-TCP, where the Si-TCP resembles, but is different from the crystallography of α-TCP (JCPDS file #9-348). All peaks within the XRD spectra could be attributed to either HA or Si-TCP and no distributions of peaks characteristic of other phases (such as β-TCP or octacalcium phosphate) were distinguishable from background.

FIG. 3 shows that as the sintering temperature was increased, the film composition changed. When the film was fired for one hour at 800° C. the composition of the film was 94% HA and 6% Si-TCP; at 900° C. there was a mixture of 62% HA and 38% Si-TCP; at 1000° C. the composition was 33% HA and 67% Si-TCP. Changes in composition and film morphology as a function of sintering duration were assessed by changing the time the thin film on quartz remained in a furnace maintained at a set temperature. A computer controlled system allowed the ramp rate and hold temperature to be defined. FIG. 4 shows that a dwell time of five minutes yielded the same equilibrium phase composition as observed after a one hour dwell time. Increased dwell time resulted in grain growth, as shown by SEM studies.

The phase composition could be modified by changing the humidity of the sintering environment while maintaining the firing conditions at 1000° C. for one hour. The reaction was suppressed by the presence of increased water vapor. Other external factors or the addition of additives to the colloid suspension did not significantly modify the results achieved for thin films on quartz.

Figure 6A:
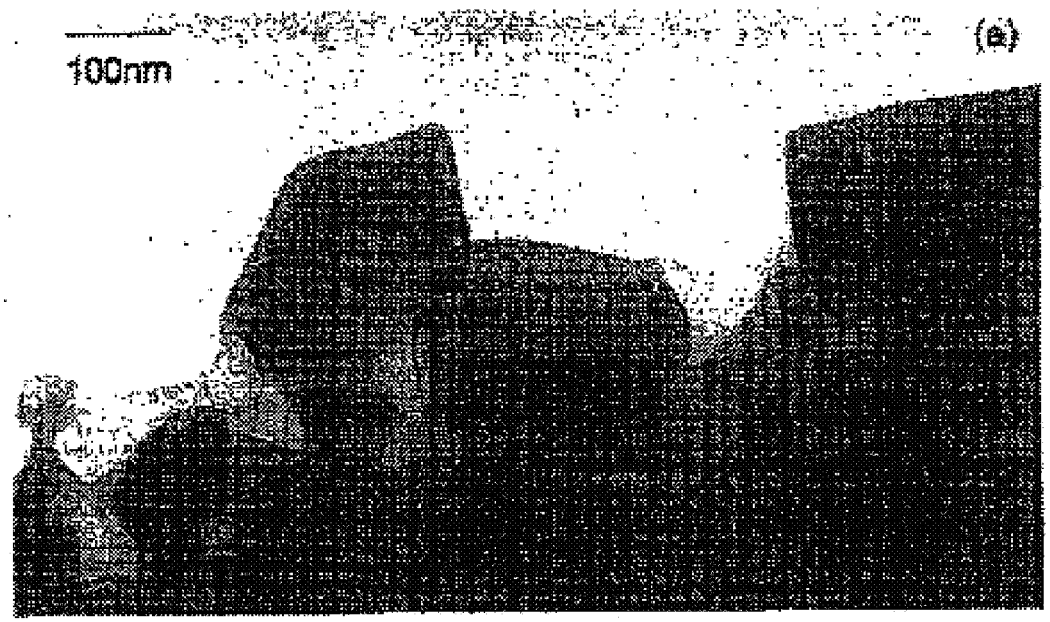
FIG. 6 is a cross-sectional TEM of a Ca—P thin film on quartz, (a) film sintered at 1000° C. (b) unsintered film; (c) EDX analysis of the sintered TEM sample at (i) the interface of the film and the substrate, (ii) the intermediate region above the interface, and (iii) the top of the film.
Figure 6B:

Optical microscopy, SEM and TEM show that the sintered films on quartz have a consistent morphology which is illustrated in FIGS. 5 and 6(a). While the films appear to be composed of translucent polycrystals under an optical microscope with phase contrast (×20), at the higher magnification achieved using an SEM (×10K) the surface morphology is that of an interconnected set of rounded particles with a high degree of porosity as seen in FIG. 5. The average dimension of these particles depends on the time and temperature of sintering. Under most conditions the mean size lies between 0.2 and 1 μm with the size increasing with the time and temperature of sintering. Cross-sectional TEM (FIG. 6(a)) of an individual particle indicates the presence of nanoporosity within the body of the particle. It is important to note that these pores were not altered with extended exposure to the electron beam, and were therefore inherent to the sample and not a sample preparation artifact. The under lying granular structure was about 5–10 nm in size. This appeared to reflect the individual granule size observed in the cross-sectional TEM micrographs of a dried but unsintered thin film on quartz as seen in FIG. 6(b).

To examine the evolution of particle agglomeration, aliquots of the colloidal suspension were analyzed for particle size after various aging times. FIG. 7 shows that a marked variation in measured particle size occurs during the 24 hour period of aging. The initial measurement gives a particle size less than 1 μm, increasing to greater than 10 μm after 8 hours, but subsequently decreasing again to approximately 1 μm after 24 hours. This is indicative of agglomeration of the fine precipitate with the most stable structure having dimensions in the range of 0.2–1.0 μm. Subsequent sintering of such agglomerates accounts both for the basic morphology of the thin films on quartz and the microporosity of bulk ceramics.

Figure 6C:
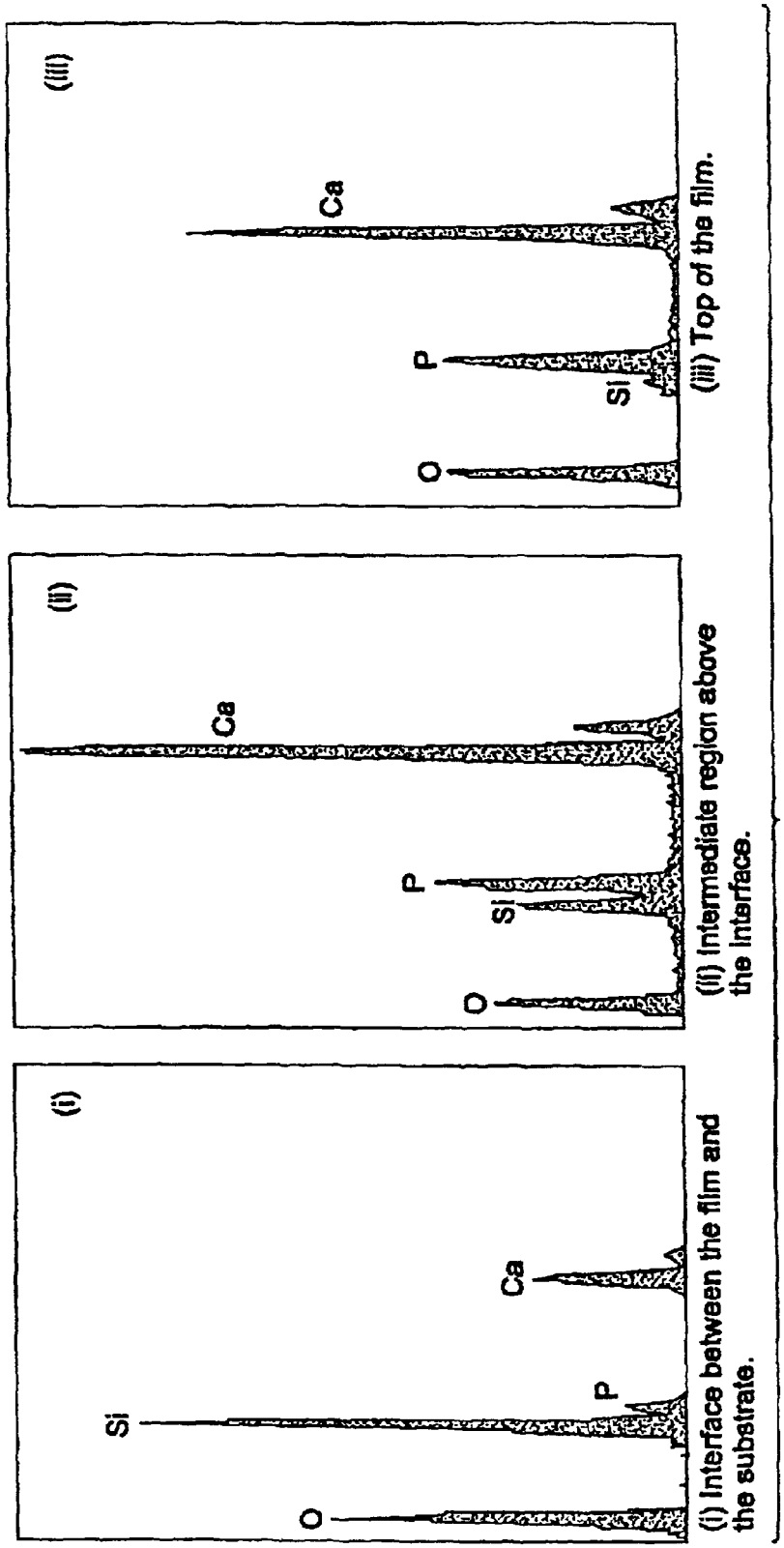

In order to understand the origin of the difference between a precipitate fired as a powder or as a thin film prepared on a quartz substrate, films on quartz were fired for 1 hour and were subsequently analyzed for elemental composition as a function of distance from the quartz interface using electron induced energy dispersive X-ray spectroscopy (EDX). As shown in FIG. 6(c)(i)(ii) and (iii) silicon was detected at concentrations which decreased with distance from the interface; however, no XRD peaks for compounds such as calcium silicate could be identified. These results suggested that Si diffusing from the quartz substrate played a role in modifying the morphology and crystallography of the thin films.

Analysis of mHA Powders with Introduced Additives

Powders prepared from the colloid of equation (1) combined with selective additives, demonstrate a unique calcium phosphate composition after sintering at 1000° C. Several possible actions of silicon as an additive in this temperature range were initially postulated such as the modification of the conversion reactions of HA into its successor compounds; the modification of the crystallographic structure of HA and its successor products by silicon substitution; and morphological changes associated with surface diffusion of the additive or by additive induced changes in surface properties.

Figure 8:
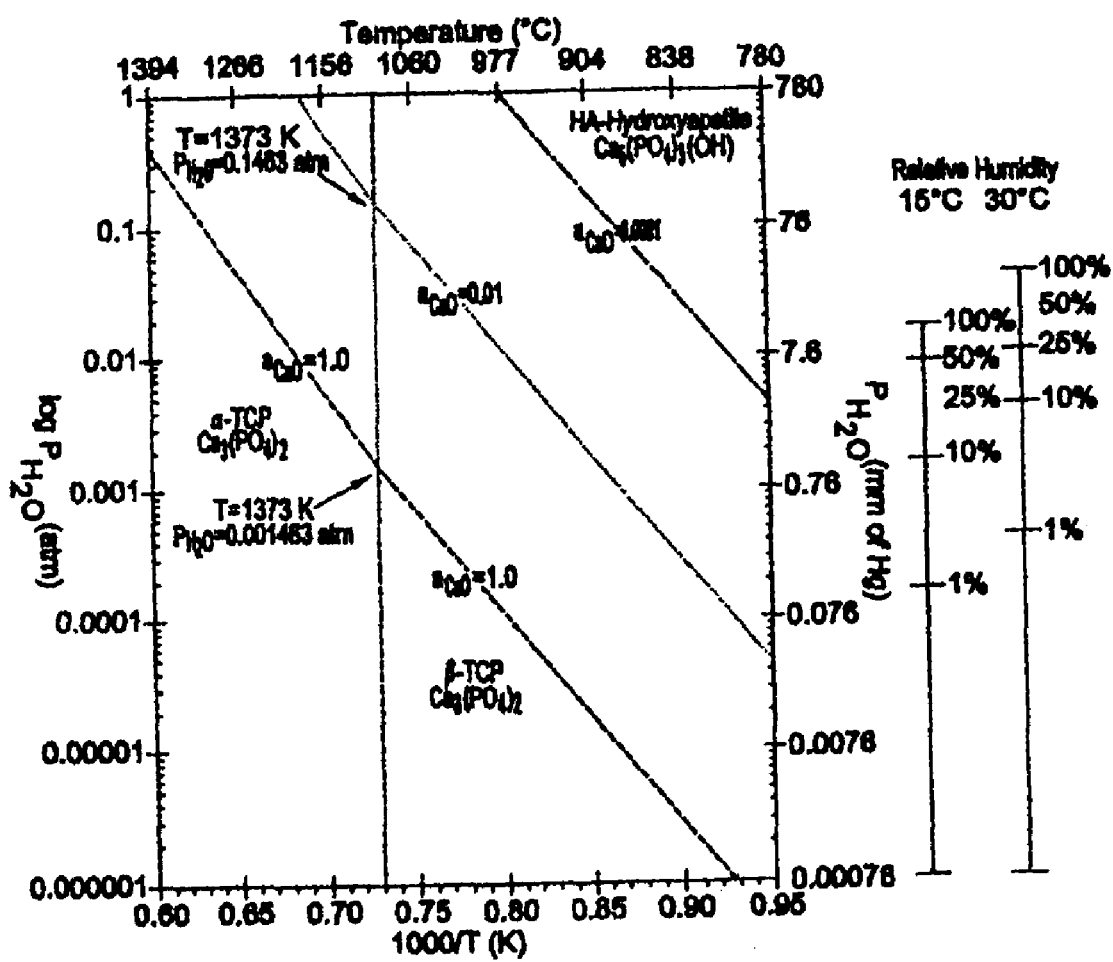
FIG. 8 shows a calculated predominance area diagram illustrating the effect of CaO activity on the relative stabilities of HA and TCP.

These possibilities were evaluated by the creation of ceramic thin films, powders and bulk materials in which processing conditions or the presence of additives changed the final products. The initial basis for defining process changes and additive selection was determined according to equilibrium thermodynamic computations using the database and programming in the Facility for the Analysis of Chemical Thermodynamics (FACT) (Bale, C. W., A. D. Pelton, and W. T. Thompson. *FACT Database* [computer program]. Contact: W. T. Thompson, Chemical and Materials Engineering, Royal Military College, Kingston, Canada, K7K 5L0 (1997). FIG. 8 shows the calculated phase diagram expected for the Ca—P system as a function of inverse temperature ($K^{-1}$) and partial pressure of $H_2O$ in the thermal processing atmosphere. The diagram applies to a closed chemical system and utilizes a large database of literature values for the Gibbs free energies of formation. The most stable phase(s) are computed for a large matrix of coordinates which lead to the placement of the phase boundaries. HA decomposes into β-TCP at temperatures below 1100° C. under low partial pressure of $H_2O$. α-TCP is formed at temperatures above about 1100° C. The predictions are consistent with high temperature crystallographic data for HA ceramics (Welch, J. and W. Gutt. *J Chem Soc* 1961; pp. 4442–4 and Schroeder, L., B. Dickens and W. Brown. *J Solid State Chem* 22 1977; pp. 253–62). The decomposition reaction, corresponding to the lowest diagonal line on the diagram, may be written as equation (2):

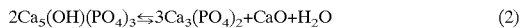

$$2Ca_5(OH)(PO_4)_3 \leftrightharpoons 3Ca_3(PO_4)_2 + CaO + H_2O \qquad (2)$$

Since the conversion of HA into TCP results in the simultaneous formation of CaO and release of $H_2O$, changes in the activity of both CaO and $H_2O$ should modify the location of the phase boundaries. The upper diagonal lines show the phase boundary when the activity of CaO is made progressively smaller. This effect can be practically accomplished by chemical combination of CaO with other compounds such as $SiO_2$. In the presence of silica ($SiO_2$), the resultant compound could be one or more of several calcium silicates. The calculations show that the decomposition boundaries in the temperature range of 800–1100° C. are in approximate agreement if CaO has the activity expected when the CaO is combined with $SiO_2$ as follows in equation (3):

$$CaO + SiO_2 \leftrightharpoons CaSiO_3 \qquad (3)$$

The most stable phosphorous-containing conversion product is, however, β-TCP. This is consistent with the widespread observation of the magnesium doped HA-based mineral whitlockite as the natural form of β-$Ca_3(PO_4)_2$ (Schroeder, L., B. Dickens and W. Brown. *J Solid State Chem* 22 1977; pp. 253–62). On the basis of the information available within the FACT database it is not possible to explain the observation of a phase similar to α-TCP as a conversion product below 1000° C. other than to assume that β-TCP is not nucleated when $CaSiO_3$ forms and that Si-TCP develops as a metastable allotropic form.

It may be noted that on the basis of chemical thermodynamics, any reaction which changes the activity of CaO should modify the phase diagram. Oxides such as $TiO_2$ have only one product with CaO as in equation (4):

$$CaO + TiO_2 \leftrightharpoons CaTiO_3 \qquad (4)$$

and may therefore be more predictable in their action. Similar calculations to those for Si showed that for a similar partial pressure of water, the phase boundary for Ti was located at a slightly lower temperature.

FIG. 9 shows that the XRD pattern for a powder prepared using an additive concentration of 1 mol $SiO_2$ to 1 mol mHA is similar to that obtained for thin films on quartz. For this sample, the silicon was added as tetrapropyl orthosilicate in 2-methoxyethanol. The spectrum was compared to JCPDS files and concluded to be a mixture of HA and Si-TCP. Subsequent experiments demonstrated that the phase composition was independent of whether the additive was introduced with 2-methoxymethanol, 2-4 pentanedione or no carrier. FIG. 10 shows the phase composition of powders sintered at 1000° C. for one hour as a function of silicon content, as determined by XRD. The phases present switch from predominantly HA to predominantly a new compound (Si-TCP) at a relative molar Si/mHA ratio of approximately 0.6. The conversion is slightly greater when powders are formed into ceramic pellets. While the specific level of conversion is dependent on processing conditions, the typical Si-TCP:HA range is 20:80 to 80:20. Due to the increased signal to noise ratio and a more linear change of the background as a function of 2θ evident in the θ-2θ XRD spectra of the powders, the accuracy of determination of the phase composition in powders is increased. Additive saturation is evident at molar ratios exceeding 1:1 indicating process constraints in the integration of further silicon. FIG. 11(*a*) shows that the crystalline morphology of a pellet formed from Si-mHA was similar to that observed in the thin films on quartz. The ceramic comprises rounded, interconnected particles of average size 0.2–1.0 μm with a large degree of localized porosity. Varying the compound preparation condition permits the formation of a range of microporous structures comprised of particles of size range 0.1 to 2.0 μm. FIG. 11(*b*) indicates that Si-mHA materials show strong evidence of osteoclastic resorption similar to that which occurs on natural bone as shown in FIG. 11(*c*).

Figure 13:
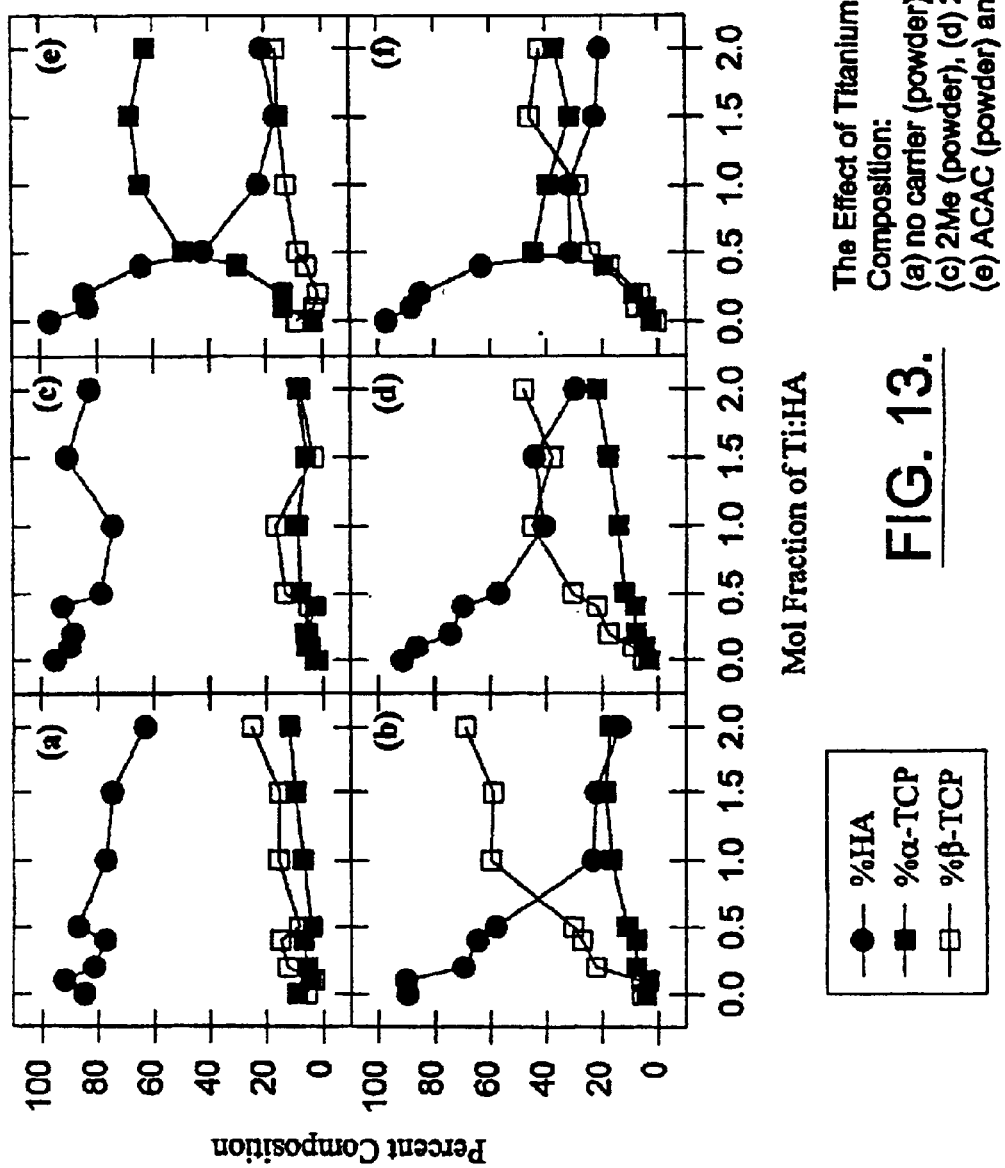
FIG. 13 shows the effect of Ti addition on mHA phase composition; (a) no carrier (powder), (b) no carrier (ceramic pellet), (c) 2Me (powder), (d) 2Me (ceramic pellet), (e) ACAC (powder) and (f) ACAC (ceramic pellet)

The XRD pattern for powders prepared using Ti as the additive also showed that conversion occurs upon addition of the Ti. However, the results were more complex as the predominant phase of TCP formed was β-TCP (FIG. 12) with the degree of conversion dependent on the carrier used with the additive. Furthermore, there was enhancement of the degree of conversion on powder grinding and processing to form ceramic pellets. The results are summarized in FIG. 13. FIGS. 13(*a*) and 13(*b*) respectively show the effects of titanium addition with no carrier for powders and ceramic pellets. Substantial conversion only occurs for pellets which were formed by grinding, pressing and resintering the original powder. The addition of titanium is similar or even less effective when 2Me is used as the carrier (FIGS. 13(*c*) and 13(*d*)). Substantial conversion at approximately 0.5 mol $TiO_2$ per mol mHA occurs in powders only when ACAC is used as a carrier and again this conversion occurs more effectively in the reground pellets, FIGS. 13(*e*) and 13(*f*). Particularly in the ceramic pellets, the phase composition shows a substantial fraction of β-TCP. The microstructure of pellets created from powders where Ti was the additive showed a particle size of approximately 0.3 μm.

The simplest interpretation of the differences between the effects of Si and Ti additives is based on the observation of the effects of additive precipitation and the changes observed in degree of conversion following powder grinding and pellet formation. In the case of Si-based additions, the degree of precipitation was essentially independent of the carrier and relatively minor changes in the degree of conversion occurred on formation into ceramic pellets. In contrast, Ti additions were ineffective when precipitation occurred when the additive was introduced into the Ca—P colloidal suspension (for no carrier and 2Me). Ti additions were effective when precipitation did not occur (for ACAC) and conversion became stronger upon grinding of the powder to form pellets and subsequent resintering. This suggests that the conversion from HA to TCP requires intimate contact between the additive and HA, possibly through surface functionalization of the precipitated mHA particles within the colloid suspension by the additive species or adsorption of the additive species on the surface of the mHA particle. When the additive and the mHA precipitate as separate species, the conversion occurs only upon strong physical inter-mixing and thermal treatment.

For comparative purposes, reference materials were prepared by equivalent thermal processing of commercially available powders (see Table 1) in an attempt to produce ceramics with a similar phase composition and surface morphology. Commercial powders were processed as pure compounds and in combination with selective additives introduced either as inorganic powders or as metallorganic species in a carrier. XRD results indicate that conversion of commercial HA (cHA) does take place, but that the primary resultant phase is β-TCP. The typical phase distribution is 73% β-TCP, 20% α-TCP and 7% HA. These results are consistent with the phase composition predicted by thermodynamics as noted in equations (2) and (3) and illustrated in FIG. 8. Of equal significance is that the surface morphology of the ceramics prepared from these powders exhibits a jagged or fractured morphology (FIG. 14b) with little interconnectedness, and a particle size an order of magnitude greater than observed in colloid-based mHA pellets (FIG. 14a). Evidence for a microporous morphology is restricted to the surface region of the particles. Pellets prepared in this fashion show no indication of resorption by osteoclasts.

The solid state chemistry of the cHA powders with introduced additives suggest that the conversion behaviour as a function of temperature, humidity and additive is consistent with equations (2)–(4). In particular, if physical mixing of the additive into the cHA powders takes place the β-TCP phase predicted by chemical thermodynamics is observed. In comparison, if intimate mixing of an unprecipitated silicon additive and a Ca—P colloid occurs the resultant phase is Si-TCP. This phase is not consistent with the predictions of equilibrium thermodynamics, but it is closely linked with the presence of Si in the Ca—P lattice. In order to use the FACT database to predict the phase boundaries for transitions to this Skelite™ compound, new values for the Gibbs free energy will be required.

The origin of the Skelite™ compound and confirmation of the mechanism of formation was investigated using techniques which assess the location of the additive within the HA or TCP structures, in an attempt to observe the presence of the reaction products predicted by equations (3) and (4).

Significantly, no calcium silicate peaks were identifiable in XRD spectra taken on either colloidal-based or mixed powder compositions where Si was the selected additive. This suggests that Si forms a dispersed or substituted phase within the phosphate lattice. Previous workers (Dickens, B. and W. Brown. *Acta Cryst B*28 1972; pp. 3056–65 and Nurse, R., J. Welch and W. Gutt. *J Chem Soc* 1959; pp. 1077–83 have suggested that calcium silicate and β-TCP form a miscible solid solution at high temperatures (>1350° C.) over the composition range of interest. The XRD spectra reported in these earlier experiments did not match that of α-TCP or the Skelite™ presently described, thus demonstrating the uniqueness of this compound. In this work, when commercially available $CaSiO_3$ was physically mixed with cHA or β-TCP powders (Table 1) and then sintered for 8 hr in alumina crucibles in air at 1250° C., the results showed that $CaSiO_3$ nucleates a crystallographic phase consistent with the Skelite™ compound (Si-TCP) (FIG. 15). The degree of conversion to Skelite™ increases as the temperature of the reaction is increased. At 1250° C. and above, depending on the amount of Si present, the powder mixtures show an increasing tendency to form a melt thus eliminating the microporous structure.

Comparison of three major peaks in the XRD spectrum of Skelite™ and α-TCP between $2\theta_{Cu}=30$ and $2\theta_{Cu}=31°$, assuming a Gaussian theoretical peak shape with a width of 0.225°, shows that there is a shift of approximately 0.1° to lower 2θ in Si-TCP (FIG. 16) resulting from an increase in the lattice parameters. The presence of this significant shift was confirmed through the close examination of the position of the HA peak present in the XRD spectra. The HA peak, $2\theta_{Cu}=31.8°$, was within 0.01° of that predicted by the JCPDS file, and hence the accurate calibration of the instrument was assured. A peak shift in the α-TCP XRD spectra to lower 2θ would occur if $Si^{4+}$ (IR=0.26 Å for CN=4) substitutes at $P^{5+}$ (IR=0.17 Å for CN=4) sites, although the effect would not be large since the lattice structure is dominated by the oxygen polyhedra of the TCP. The fact that the substitution reaction occurs at 1000° C. only for colloidal particles in which the Si is chemically functionalized on the surface suggests that the substitution kinetics are very slow in the low temperature range.

Nuclear Magnetic Resonance Studies

Figure 17A:
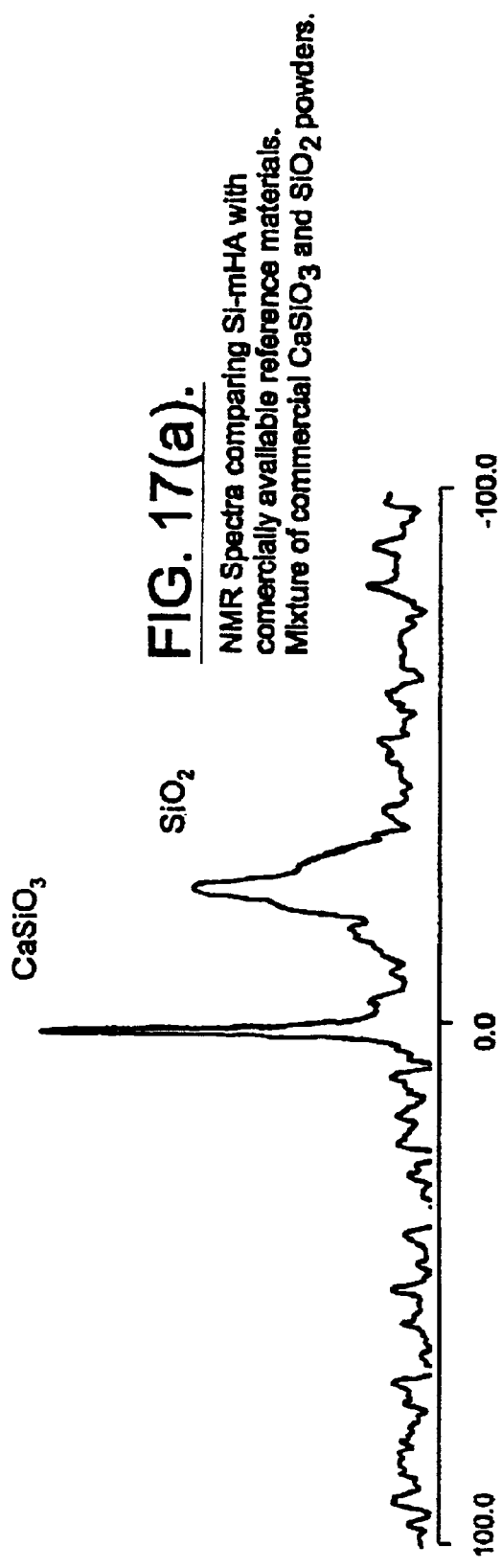
FIG. 17 shows the NMR spectra comparing Si-mHA with commercially available reference materials; (a) mixture of commercial $CaSiO_3$ and $SiO_2$ powders, (b) Si-mHA powder.
Figure 17B:
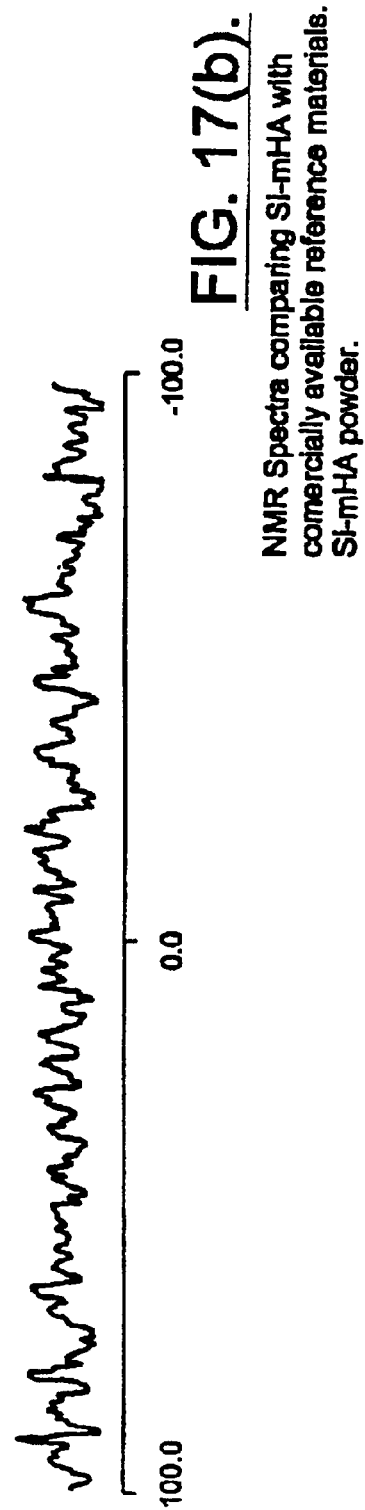

Magic-angle NMR studies were carried out on Si-mHA powders. Comparisons were made with simple physical mixtures of cHA, α- and β-TCP, $CaSiO_3$ and $SiO_2$ in proportions similar to the phases present in the Si-mHA powders. For Si-mHA, no Si signals could be observed under any conditions of measurement. Careful comparison with signals measured on $CaSiO_3$ and amorphous $SiO_2$ was used to set the lowest level of sensitivity at which the compounds or local structures could be measured. FIG. 17 compares NMR spectra, signal averaged over 120,000 pulses, for Si-mHA with that obtained from a simple physical mixture of cHA and 10% of equal parts of $CaSiO_3$ and $SiO_2$. The absence of any NMR signal in the Si-mHA indicates that Si is highly dispersed throughout the crystallographic structure of mHA so that no clearly definable location or compound could be identified.

Infrared Spectroscopy Studies

FIG. 18 compares infrared spectra for sintered powders of (a) cHA, (b) mHA, and (c) Si-mHA. The peak pair found at the lowest wave numbers near 600 $cm^{-1}$ indicate the presence of similar but not identical bonds. The spectra for cHA and mHA powders (no additives) were otherwise generally similar. Silicon addition causes a substantial narrowing of the P—O stretch peak and a shift in its position from 1048 to 1065 $cm^{-1}$ (FIG. 19).

In order to assess these changes, IR spectra of $CaSiO_3$, CaO, $SiO_2$ and commercial β-TCP were examined. The $CaSiO_3$ spectrum shows a series of distinctive peaks at 717, 563 and 434 $cm^{-1}$ that are not apparent anywhere in the spectra for Si-mHA powders. The CaO spectrum has a strong sequence of bands below 463 $cm^{-1}$ which are also not observed in the Si-mHA spectrum. The $SiO_2$ spectrum shows a very strong, well-resolved peak at 1104 $cm^{-1}$ characteristic of the Si—O bond. An interpretation of the Si-mHA spectra is that the Si—O bond absorption occurs at lower wave numbers than in the pure $SiO_2$. The apparent shift in the P—O stretch can be explained by the growth of a Si—O peak. It is logical that the Si—O and P—O peaks would occur at similar positions since silicon and phosphorus are located beside each other in the periodic table and have similar ionic radii. The fact that the P—O peak appears to shift further indicates the formation of a new silicon compound, Skelite™.

A structural model for silicon substitution based on the IR analysis is a crystal lattice of TCP-like and HA-like material with molecular dispersion of silicon throughout the lattice. This is consistent with the NMR and XRD results. The narrowing of the P—O peak suggests the existence of a less broad distribution of types of P—O bonds within the structure or an increase in crystallinity compared to the mHA with no introduced additives.

In Vitro Bone Cell Activity Studies

Figure 20:
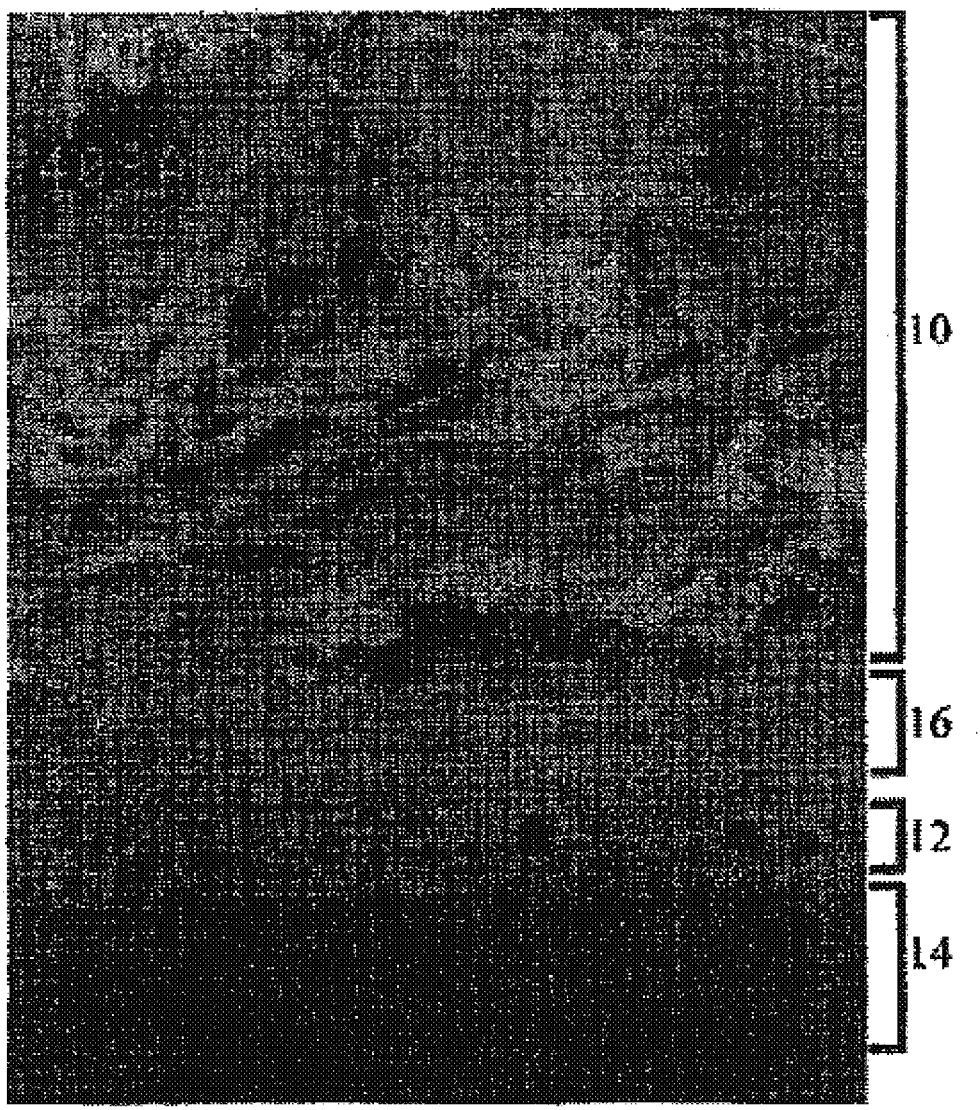
FIG. 20 is a cross-sectional SEM micrograph illustrating mineralized collagenous matrix deposited on a thin film of the stabilized composition.

The Skelite™ compound on a substrate may be used to assess the resorptive activity of osteoclasts and monitor the change in this level of resorptive activity either as a result of a disease process or the inclusion, in the culture medium, of an agent such as a drug which would influence, either directly or indirectly, osteoclastic resorptive activity. As provided as a film on a substrate, the compound is also suitable for the culture of active osteoblasts in order to observe and assess the secretion of mineralized matrix thereon. As shown in FIG. 20, mineralized collagenous matrix 10 is deposited by cultured osteoblasts on the surface of the stabilized thin film 12 as provided on a quartz substrate 14. A well integrated boundary layer 16 resembling a cement line is shown which is similar to the same type of cement lines formed by osteoblasts in vivo at the interface between new bone and old bone. This clearly suggests that the biomaterial compound allows for physiological osteoblast activity further supporting the role of the compound as an important product that can participate in the natural bone remodeling process.

Figure 22A:
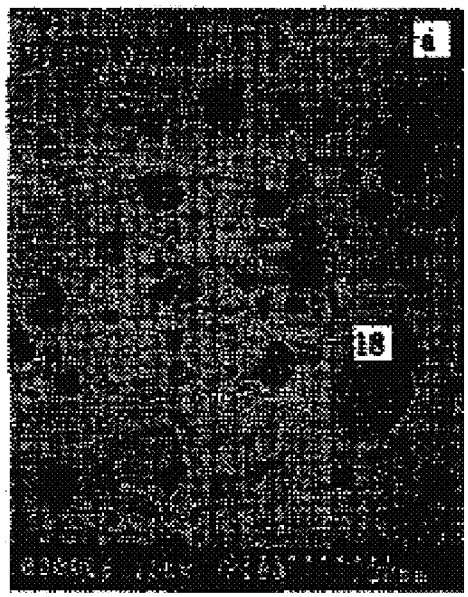
FIGS. 22(a) and (b) are SEM micrographs of osteoclast resorption pits on thin films of the stabilized composition.
Figure 22B:
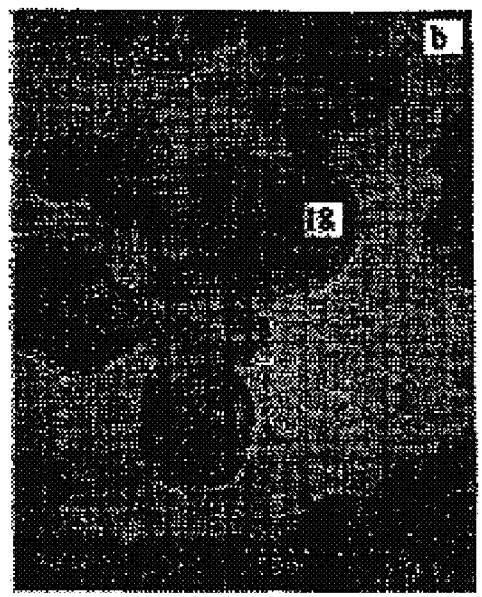

The thin film devices may be used as a means of quantifying the resorptive activity of osteoclasts or the formation of mineralized matrix by the activity of osteoblasts. Such activity analysis may occur under continuous real-time monitoring, time-lapse intervals or end-point determination. The steps in establishing bone cell activity are common to each of the above monitoring schedules in that bone cells (either animal or human) are cultured, in specific conditions, on one or more of the thin film devices. The culture period is from several hours to many days and preferably from approximately 2 to 10 days (the optimum time is cell species and protocol dependent), during which time the extent of osteoclast activity may be continuously monitored, periodically monitored, or simply not monitored on an on-going basis in favour of final-end-point determination. FIGS. 11(B) and 22 illustrate osteoclast resorption pits on ceramic pellet and thin film formats of the Si-TCP compound.

Figures 21A, 21B:
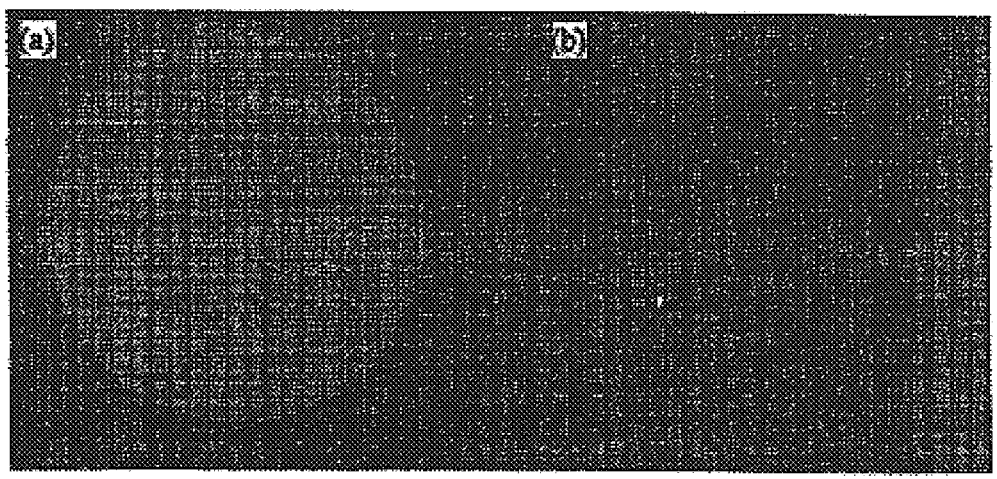
FIG. 21 are photographs of fluorescence analysis (a) is the deposition of fluorescent mineralized matrix produced by osteoblasts cultured on the stabilized composition, (b) is a control in which no osteoblasts are cultured on the stabilized composition and no fluorescent mineralized matrix is visualized.

Similarly, osteoblast activity may be quantified by measuring the amount of mineralized matrix deposition. As is shown in FIG. 21(a), a quartz disc coated with a stabilized film of the present invention and simultaneously cultured with osteoblasts in the presence of culture medium containing tetracycline, a natural fluorescent material, displays fluorescence indicating the presence of mineralized matrix. In contrast, a stabilized film coated on a quartz substrate in the presence of medium containing tetracycline but no osteoblasts (FIG. 21(b)) shows no fluorescence. As the cells take up tetracycline, it is metabolized and incorporated into the newly formed mineralized matrix. The amount of mineralized matrix is proportional to the measurable fluorescence emitted. This demonstrates that osteoblasts actively secrete mineralized matrix on the stabilized composition.

The Skelite™ Compound

The significant correlations with cell-based bioactivity and resistance to dissolution at normal physiological pH 6.4 to 7.3 are the presence of the additive stabilized compound and the microporous morphology. The morphology is accounted for by the sintering of particles of average size 0.2 to 1.0 µm. The presence of a Si-TCP phase that is essentially insoluble in biological media at low temperature using silicon as the introduced additive is unexpected and is induced by the distribution of Si substituted throughout the structure. Considering that the underlying structure of the particles is the agglomeration of granules of size range of approximately 1 to 20 nm, uniform dispersion of the silicon additive and functionalization of the surface of an individual granule is assured by permeation of the silicon sol throughout the agglomerate. The key aspect of this investigation was the determination that silicon does not induce an α-TCP phase resulting from the decomposition of HA, but rather it creates a Si-TCP phase, a new biomaterial compound, by substitution of silicon at phosphorus sites. The fact that silicon induces a Si-TCP compound can now be explained through the crystallography of the calcium-phosphate system and the defect chemistry associated with silicon substitution into the Ca—P lattice. One skilled in the art would understand that other additives having an ionic radius which is different to that of silicon as described herein, but may still substitute into the Ca—P lattice is also embodied for the compound of the present invention. Therefore the compound is not restricted only to silicon as the additive.

It is important to note that "effective ionic radius" has been selected as the term of reference in these studies (Shannon, R. D., Acta Cryst. A32., 751, (1976). The ionic radius specifications provided herein reflect the effective ionic radius for coordination numbers of 4, 6 or 8. It is apparent to those skilled in the art that "ionic crystal radius" may also be used in the practice of the present invention and thus may be used to define equivalent specifications for the compound and the formula of the compound as described herein. A summary of the effective ionic radius and the ionic crystal radius for various elements is provided in Table 2.

When substituting Si in the HA lattice, the ionic radius of $Si^{4+}$ (IR=0.26 Å for CN=4) suggests that $Si^{4+}$ can enter at $P^{5+}$ (IR=0.17 Å for CN=4) sites within the $PO_4^{3-}$ tetrahedra although it could also be included at $Ca^{2+}$ (IR=1.0 Å for CN=6) sites. The lattice strain and compensating defect will be significantly different in the two cases and the effects of covalency will substantially modify the result. A low temperature substitution of $Si^{4+}$ into $P^{5+}$ sites creates less strain and accommodates the covalency well. The radius ratio for silicon and oxygen is consistent with that required for the tetrahedral coordination of silicon in an oxygen lattice. Such a substitution requires the formation of a single positively charged defect for charge compensation. An obvious defect is one oxygen vacancy for every two silicon ions, although the energy required to displace oxygen-phosphorous bonds within an already formed $PO_4^{3-}$ tetrahedron may be substantial. Theoretically, substitution of an ion with an appropriate ionic radius and a valence of ≧3 at $Ca^{2+}$ sites could also provide charge compensation. Such elements may include Ce, La, Sc, Y and Zr. Restrictions on the use of particular elements may be present due to the particular applications for use as a biomaterial.

In the formation of the Si-TCP compound, compositional analysis suggests that the Ca:P ratio decreases from approximately 1.67 (HA) to 1.5 (TCP). This could be induced by (1) the removal of calcium from the lattice, or (2) the introduction of additional phosphorous or an element that substitutes for phosphorous. A reduction in the calcium content of the lattice could theoretically occur by the formation of calcium silicate distributed within the structure. However, no evidence of calcium silicates as a well defined compound can be found in either the NMR or the IR results. Thus extensive silicon substitution must occur forming a multitude of Si-substituted P—O sites in the lattice.

In the case of $Ti^{4+}$, the ionic radius of (IR=0.42 Å for CN=4) likely precludes its substitution at $P^{5+}$ sites and it must therefore enter the crystal at more general interstitial sites within the lattice. Since titanium has been demonstrated to be less effective in modifying the crystal structure to create a stabilized TCP, this suggests that the nucleation of the Si-TCP phase is intimately connected with the substitution of silicon at phosphorous sites. In particular, the observed phase being in fact a Ca—P—Si compound with a crystallographic structure similar but different from α-TCP rather than pure α-TCP, resolves conflicts with respect to the new compound's decreased solubility and the predicted decomposition phase diagram.

The crystallography of the Ca—P phase diagram has been extensively studied and compared (Elliott J. *Structure and Chemistry of the Apatites and Other Calcium Orthophosphates* New York: Elsevier (1994) in apatites (Elliott, J. *Nature Physical Science* 230 1971; p. 72), β-TCP (Dickens, B., L. Schroeder and W. Brown. *J Solid State Chem* 10 1974; pp. 232–48 and Labarther, J., G. Bonel and G. Montel. *Ann Chim (Paris)* 14th Series 8 1973; pp. 289–301) and α-TCP (Calvo, C. and R. Gopal. *Am Miner* 60 1975; pp. 120–33). Significant differences have been noted between the structures of α and β-TCP (Elliott J. *Structure and Chemistry of the Apatites and Other Calcium Orthophosphates* New York: Elsevier (1994) and Calvo, C. and R. Gopal. Am Miner 60 1975; pp. 120–33) and equally significant similarities have been seen between α-TCP, apatites and calcium silico-phosphate compounds via the glaserite structure (Mathew, M., W. Schroeder, B. Dickens and W. Brown. *Acta Cryst* B33 1977; pp. 1325–33). A primary component of the phosphate lattice is the presence of $PO_4^{3-}$ tetrahedra, although these structures can vary considerably throughout a complex lattice. For example, in α-TCP the P—O distances vary from 1.516 to 1.568 Å and the O—P—O angles vary from 104.1 to 115.2° (Calvo, C. and R. Gopal. *Am Miner* 60 1975; pp. 120–33). Substitution of a Si at such sites implies a range of environments for such an additive.

Following Elliott (Keller, L., P. Rey-Fessler. *Characterization and Performance of Calcium Phosphate Coatings for Implants* edited by E. Horowitz and J. Parr. Philadelphia: ASTM, pp. 54–62 (1994) the space group of HA has three kinds of vertical or columnar symmetry. There are columns of $Ca^{2+}$ ions spaced by one half of the c-axis parameter along three-fold axes which account for two-fifths of the $Ca^{2+}$ ions in the structure. These ions are given the designation Ca(1). The $Ca^{2+}$ ions are linked together by $PO_4$ tetrahedra in which three oxygen atoms come from one column and the fourth comes from an adjacent column. The result is a three-dimensional network of $PO_4$ tetrahedra with enmeshed $Ca^{2+}$ ions, and channels that contain the residual calcium, Ca(2), and ions such as $OH^-$ which make up the HA structure.

The α-TCP structure also comprises columns of $Ca^{2+}$ and $PO_4^{3-}$ ions parallel to the c-axis (Elliott, J. *Nature Physical Science* 230 1971; p. 72). The columns are actually anion-anion columns . . . CaCaCaCa . . . and cation-anion columns . . . $PO_4$Ca $PO_4$ $PO_4$Ca $PO_4$ $PO_4$Ca $PO_4$ . . . where is a vacancy (Elliott J. *Structure and Chemistry of the Apatites and Other Calcium Orthophosphates* New York: Elsevier (1994)). The presence of this vacancy may facilitate the creation of $O^{2-}$ vacancies in neighboring $PO_4^{3-}$ tetrahedra required to accommodate the substitution of $Si^{4+}$ at P5+ sites. Analogous cation-anion columns occur in glaserite, $K_3Na(SO_4)_2$, except that the vacancy is occupied by a $K^+$ ion. Strong similarities exist between the glaserite and apatite structures (Dickens, B. and W. Brown. *Acta Cryst* B28 1972; pp. 3056–65). The apatite structure can be derived from that of α-TCP by replacing cation-cation columns at the corner of the apatite unit cell by anion columns ($OH^-$ or $F^-$). The remaining cation columns in α-TCP become the columnar Ca(1) ions in apatite, whilst the $PO_4^{3-}$ and $Ca^{2+}$ ions that form the cation-anion columns in α-TCP have approximately the same positions as the $PO_4^{3-}$ and Ca(2) ions in apatite. Of significance to this analysis is that the glaserite structure is related to silico-carnotite $Ca_5(PO_4)_2SiO_4$ (Labarther, J., G. Bonel and G. Montel. *Ann Chim (Paris)* 14th Series 8 1973; pp. 289–301) and —$Ca_2SiO_4$ (Calvo, C. and R. Gopal. *Am Miner* 60 1975; pp. 120–33). This is consistent with the report that the system $Ca_2SiO_4$—$Ca_3(PO_4)_2$ forms a continuous series of solid solutions at higher temperatures based on the glaserite structure (Nurse, R., J. Welch and W. Gutt. *J Chem Soc* 1959; pp. 1077–83).

In contrast, there are no such similarities between the structure of HA and β-TCP. The β-TCP structure is a distortion of the parent lattice, $Ba_3(VO_4)_2$, with layers perpendicular to the c-axis. There is no columnar relationship between cations in the structure. Because of the size of the $Ca^{2+}$ ion, there is a reduction in the number of $PO_4$ tetrahedra in the structure compared to that for the parent lattice and a reduction in the number of formula units within the hexagonal unit cell. Two types of Ca sites exist within the β-TCP unit cell: those known as Ca(5) are fully occupied, while a particular set of cation sites known as Ca(4) are only half occupied (Elliott J. *Structure and Chemistry of the Apatites and Other Calcium Orthophosphates* New York: Elsevier (1994)). Upon doping TCP with $Mg^{2+}$ (IR=0.72 Å for CN=6) the Mg distributes itself first randomly on the Ca(4) and Ca(5) sites, but subsequently only substitutes at the Ca(5) sites. Because $Mg^{2+}$ is smaller than $Ca^{2+}$ (IR=1.0 Å for CN=6) and the original distortion of the $Ba_3(VO_4)_2$ structure occurred because $Ca^{2+}$ is smaller than $Ba^{2+}$ (IR=1.35 Å for CN=6), the β-TCP structure is stabilized with the addition of $Mg^{2+}$ to form the naturally occurring mineral, whitlockite (Calvo, C. and R. Gopal. *Am Miner* 60 1975; pp. 120–33). Indeed the addition of Mg to β-TCP at high temperatures tends to stabilize the structure well into the α-TCP range. In the case of the addition of an ion such as $Ti^{4+}$, the slightly larger ionic radius (IR=0.61 Å for CN=6) would suggest that it would also be accommodated by substitution at Ca(5) cation sites with results that are less defined than for $Mg^{2+}$. Since charge compensating defects are necessary, the stabilization or creation of $Ca^{2+}$ vacancies on Ca(4) sites would serve this purpose. Therefore substitutional Ti should stabilize the β-phase once TCP has been formed.

A feature of the presently characterized compound is that the Skelite™ structure is only achieved when intimate contact occurs between the precipitate and the additive. When silicon is introduced into already formed and fired powders at relatively low temperatures, the resulting post-sintered phase is predominantly β-TCP. In this case the silicon plays a role similar to that described for titanium above and simply acts to reduce the activity of CaO in the decomposition of HA under the terms of equation (3). In the case of colloidal powders precipitated in close association with an additive such as silicon, both the surface activity will be high and strongly functionalized complexes will be formed in the solution and at the interfaces of the precipitated granules. Through sintering, a range of $PO_4^{3-}$ and $SiO_4^{4-}$ tetrahedra will be established along with the necessary oxygen vacancies. In this case, nucleation of the glaserite-based Si/P phase will take place. While previously this was interpreted as a form of α-TCP it is, in fact, an entirely different compound with its own values for solubility and bioactivity (Si-TCP). Thus the crystal phase composition, surface morphology and bulk morphology originates from the chemically active and agglomerated state in which the starting material is precipitated, and the degree to which this state controls the location at which the $Si^{4+}$ cation is substituted.

Again, although silicon has been the most extensively studied and appears to be the preferred substituted element of the invention, it is apparent to one skilled in the art, that any additive that can enter and distribute throughout the crystal structure of the calcium phosphate lattice and result in the compound of the present invention can be substituted for silicon. Therefore, the present compound is not restricted to only silicon as the substituted element but may also include other suitable elements having a suitable ionic radius of approximately 0.1–0.4 Å such as for example boron. It is also understood that other additives in addition to the silicon or boron may also be present in the compound of the present invention. Such-elements may also form part of the Ca—P lattice where such elements and/or the amount of oxygen may act to balance charge compensation for additives incorporated into the compound. Such additives may be selected from the group consisting of Ce, La, Sc, Y, and Zr.

It is also understood by those skilled in the art that the novel compound of the present invention can be combined with a calcium phosphate material such as calcium hydroxyapatite, α-TCP, β-TCP, octocalcium phosphate, tetracalcium phosphate, dicalcium phosphate, calcium oxide and other like materials. The resultant combination can be as a physical mixture or as a solid solution. In addition, other additives such as polymers or microfibers may additionally be added to the compound of the present invention to increase mechanical strength and toughness. The particle size of these additives may be selected such that the additive may be removed through phagocytosis by the action of macrophages. Metals may also be present in combination with the present compound to form composite structures. Such structures are also intended to be embodied in the present invention.

The Skelite™ Morphology

The morphology of the synthetic stabilized calcium phosphate compound (Skelite™) is unique and has not been previously reported or demonstrated. We have now demonstrated a morphology presenting an interconnected globular structure of rounded particles having an interconnected microporosity. In accordance with a preferred aspect of this invention, the morphology successfully supports cultures of functional osteoclasts and osteoblasts.

The surface morphology of the coating has a characteristic form involving a interconnected globular structure (FIG. 6a). The size of the particles varies from approximately 0.2–1 μm in lateral dimension. This morphology may allow for the percolation of liquid media and other physiological fluids within the coating. In contrast, the surface morphology of hydroxyapatite prepared from other methods, does not result in a structure as provided by the present invention. In addition, is has been reported that synthetic polycrystalline hydroxyapatite is not resorbed by osteoclasts (Shimizu, Bone and Minerology, Vol. 6, 1989).

The globular morphology is made up of rounded particles comparable in size to the aggregated deposits initially made by an osteoblast cell in the process which leads to bone formation. The present composition provides a morphology compatible with the type of morphology bone cells encounter in vivo. Particularly, the size and shape of the cell/compound interface facilitates bone cell attachment. Such attachment is a necessary precursor to normal bone cell activity.

The bulk microporosity of the synthetic stabilized calcium phosphate compound may ensure that the calcium or phosphate ion concentrations near the surface of the artificial material are within the limits expected by the cell as encountered in vivo with natural bone which is made up of hydroxyapatite, collagen and other fibrous tissues. During osteoclast mediated extracellular dissolution processes which lead to resorption, this complex material leads to a particular local concentration of dissolution products.

The bioactive synthetic biomaterial ompound of the present invention provides a unique chemical composition together with a unique morphology and internal microporous structure that has never previously been demonstrated. Compositions have not been previously reported which demonstrate consistent bone-cell bioactivity in vivo and in vitro in which bioactivity in vitro can be readily, accurately and repetitively quantified. The nature of the stabilized biomaterial compound is versatile in that it can be provided in a fine or coarse powder, pellets, three-dimensional shaped pieces, macroporous structures, thin films and coatings. In each case, the unique morphology and internal microporosity is maintained as well as the stabilized calcium phosphate composition.

In summary, a new calcium phosphate-based biomaterial compound has been created and specifically characterized. This new biomaterial exhibits two prominent features:

(1) A unique composition created by the introduction of additives, such as silicon, into the colloidal precipitate to form upon sintering a stabilized calcium phosphate phase comprising the novel compound.
(2) A characteristic microporous morphology that arises from the agglomeration of particles within the colloid precipitate and the sintering of the material to produce a network of interconnected particles.

It is now revealed via numerous difficult analytical tests and complex data interpretation that this stabilized calcium phosphate compound is a novel additive stabilized structure referred to as Skelite™ that may exist in combination with HA, α-TCP, β-TCP or other suitable calcium phosphate phases. This new compound has been characterized to have the formula, $(Ca_{1-w}A_w)_i[(P_{1-x-y-z}B_xC_yD_zO_j)]_2$, wherein A is selected from those elements having an ionic radius of approximately 0.4 to 1.1 Å; B, C and D are selected from those elements having an ionic radius of approximately 0.1 to 0.4 Å; w is greater than or equal to zero but less than 1; x is greater than or equal to zero but less than 1; y is greater than or equal to zero but less than 1; z is greater than or equal to zero but less than 1; x+y+z is greater than zero but less than 1; i is greater than or equal to 2 but less than or equal to 4; and j equals 4−δ, where δ is greater than or equal to zero but less than or equal to 1. The terms w and δ may be selected to provide charge compensation of the elements present in the compound.

An important processing step involves the intimate mixing of silicon as a candidate additive with the particles of the colloidal suspension to ensure the local availability of reactants. This in combination with the similarity of the silicon and phosphorous ionic radii, creates an environment favorable for silicon substitution at phosphorous sites within the Ca—P lattice and the development of the silicon-stabilized TCP structure.

The unique composition does not occur in the absence of intimate mixing as the effect of added silicon in these circumstances is only to influence the activity of CaO as an HA decomposition product. Similarly, the use of additives comprised of larger ions, such as titanium, cannot be accommodated in the lattice at phosphorous sites thereby precluding the important phosphate substitution phenomenon. In both of these cases, the resulting product is predictably β-TCP.

In view of the ability of Skelite™ to participate in the natural bone remodeling process, significant opportunities exist for the development of synthetic bone grafts and bone repair products that are indeed bioactive.

Synthetic Bone Graft Applications

A synthetic bone graft that comprises in whole or in part the novel compound of the present invention has numerous applications in the orthopedic industry. In particular, there are applications in the fields of trauma repair, spinal fusion, reconstructive surgery, maxillo-facial surgery and dental surgery.

The gold standard in the industry for treating traumatized bone is an autologous bone graft, commonly referred to as an autograft. Autograft transplants involve a surgical procedure in which healthy bone is taken from an alternate part of the patient's skeleton to repair areas of skeletal trauma. Autografts however, require double surgical procedures; one for graft removal and a second for re-implantation at the damaged site. This makes the procedure very expensive and time consuming. Additionally, it is not uncommon for patients to subsequently suffer chronic pain at the autograft harvest site.

Another widely used bone graft technique is the use of allograft, a term referring to a tissue graft from another individual or animal. In this situation, bone is removed from the donor and implanted in the patient. Allografts are susceptible to various negative consequences. For example, the use of allograft from an animal other than a human carries the possibilities of cross species infection and immunological rejection. Even human sourced allograft, which is used more often than animal tissue, exposes the implant recipient to the possibilities of rejection and disease.

The use of Skelite™ eliminates the pain and costs associated with the bone harvest procedure required in autograft transplants. Furthermore, since Skelite™ is generated in a laboratory and is completely synthetic, it removes the possibility of transmission of infection and disease, as well as eliminates sources of immunological rejection by the patient.

Skelite™ fulfils the need for a versatile bone reconstruction material. Its ability to immediately stimulate local natural bone growth provides stability and rapid integration, while the body's normal cell-based bone remodeling process slowly resorbs and replaces the implant with natural bone. This removes the concerns of long term compatibility and durability associated with current artificial implant technologies.

Products formed from Skelite™ will involve different configurations in order to address the requirements of particular applications. For example, Skelite™-based products can be manufactured as a fine or coarse powder, pellets, shaped three dimensional pieces, macroporous structures, thin films and coatings. In addition, these products could potentially carry an integrated bone growth factor to speed short term recovery.

The use of Skelite™ in a macroporous configuration allows the open porous structure to serve as a scaffold for the integration of new bone tissue. The macroporous structure is formed by the coating of the compound onto a reticulated polymer and subsequently removing the polymer through pyrolysis. The macroporous structure comprises an open cell construction with interconnected voids having a pore size of approximately 50 to 1000 micron. Due to this design, Skelite™ is the ideal bone substitute for implantation at defect sites where special measures are required to encourage new bone growth to bridge areas of major tissue loss due to trauma or surgical intervention. The Applicant has identified two primary approaches for the clinical use of such a product: direct implantation and tissue engineering.

Direct Implantation

The simplest approach is to directly implant the Skelite™ scaffold at the location of skeletal trauma where the bioactive properties of the biomaterial compound stimulate the body's natural bone repair mechanism. Once the initial healing process is complete, the Skelite™ scaffold is progressively replaced with natural bone as part of the body's orderly remodeling process.

Hybrid versions of Skelite™-based products are possible where bone growth factors are incorporated into the scaffold as a post-manufacturing process or at the time of surgery. The availability of the growth factor at the repair site increases the rate of new bone formation thereby improving patient recovery time and lowering overall health care costs.

Tissue Engineering

The concept that underlies the tissue engineering application is to remove bone cells from the patient's skeleton using an established bone marrow aspiration technique, and then carefully introduce the collected cells (cell seeding) into the open cell structure of the Skelite™ scaffold in a sterile biotechnology facility. The cells and scaffold are then incubated so that the cells have an opportunity to multiply and begin to fill the scaffold with new mineralized matrix. After several weeks, the biological implant is ready for implantation back into the patient. This biotechnology bone growth process is termed "tissue engineering", and the procedure serves to enhance the ability of surgeons to reconstruct severely compromised areas of the skeleton. Once successfully integrated at the repair site, the Skelite™ implant is subsequently remodeled into natural bone by the ongoing activity of bone cells.

A refinement of this approach is to selectively extract and multiply in cell culture only special precursor cells termed Mesenchymal Stem Cells (MSCs). In order for these cells to remain healthy during biological processing, they need to be attached to a suitable physical carrier. In addition, the performance of the cells can benefit from the addition of organic bone growth factors. Skelite™ is a suitable carrier since it allows for both the integration of bone growth factors and the attachment of specialized MSCs. In addition, following implantation and patient recovery, the Skelite™ scaffold is subsequently remodeled into natural bone.

The use of Skelite™ in direct implantation or tissue engineering applications has important advantages over the use of naturally sourced bone graft material, and consequently Skelite™ products have the potential to replace the autograft procedure as the orthopedic surgeon's preferred treatment strategy.

The key advantages of implantable products formed from the Skelite™ material are:

Immediately stimulates local natural bone growth at the implanted site, thus providing early stability and full integration.

Ensures long term biocompatibility and efficacy.

Acts as a bioactive scaffold for use in advanced tissue engineering applications.

Eliminates the cost and chronic pain associated with the double surgical procedures required in traditional autograft transplants.

Eliminates the risks of immunological rejection and infection transmission.

Meets the needs of various orthopedic applications, as the product is available in different configurations.

Allows for the use of growth factors that can further increase the rate of natural bone healing and subsequent remodeling.

Provides a means for timed-release drug delivery.

Disappears naturally through the body's bone remodeling process once therapeutic function is complete.

Drug Carrier Application

The Skelite™ biomaterial may also be used for the incorporation of selected pharmaceuticals into the compound for the further enhancement of the bone healing and remodeling processes. In this respect, pharmaceuticals that have been incorporated into the Skelite™-based products can be predictably released at the site of implantation and hence become available to assist in the bone regeneration process. The Skelite™ biomaterial may also be designed as a slow release vehicle for appropriate pharmaceutical compounds.

Primary candidates for incorporation into Skelite™-based products are selected bone growth factors. These proteins have been identified as being critically important in growing and maintaining healthy bone tissue. In particular, when applied at the site of traumatized bone, natural bone growth is enhanced with a corresponding improvement in overall therapeutic response. However, a compatible carrier system is required to deliver such therapeutic biologicals to the site and ensure local release of appropriate concentrations of the drug. Implant studies have shown that products formed from the Skelite™ biomaterial are suitable for use as drug carriers. One skilled in the art would understand that other pharmaceuticals such as antibiotics for example which may aid in the bone healing process may also be incorporated into the Skelite™ compound.

Coating Applications

Through a liquid application process, the Skelite™ material can be coated on to orthopedic and dental implants to improve and promote natural bone fixation and to improve long term implant stability. Such a coating of approximately 0.1 to 10 μm acts at the interface with the patient's own tissue to promote natural bone growth during the weeks immediately following surgery, and is then progressively replaced by the ongoing activity of bone cells once the initial healing process is complete. The result is a strong union between the implant and the host bone. This is not the case with conventional calcium phosphate implant coatings where the biologically inert coating is subject to mechanical detachment (delamination) from the metal substrate, causing potentially catastrophic implant failure.

The key advantages of an implant coating formed from the Skelite™ material are:

Promotes rapid natural bone growth during the recovery period and is then progressively replaced through the body's orderly remodeling process.

Eliminates the coating as a potential source of long-term failure and reduces the risk to the patient of incurring complicated and costly revision surgery.

Reduces patient recovery time and associated health care costs.

Permits a strong union directly between the implant and the patient's natural bone.

Involves a manufacturing process based on a liquid application procedure which allows full coverage of the device, including complex surface geometries.

In Vitro Diagnostic Applications

As a thin film as provided on a suitable substrate, the Skelite™ compound significantly advances the study and understanding of bone cell functional properties. The composition and morphology of the stabilized film, as provided in accordance with this invention, permits the culture of various types of bone cells thereon. The properties of the film may be adjusted to encourage a significant degree of resorption of the Si-TCP compound of the film material through to a negligible degree of resorption of the Si-TCP compound in the study of osteoclast activity. Similarly, osteoblast activity may be studied by detecting the deposition of mineralized matrix. The ability to provide the material in a film format which is sufficiently thin that resorption of the Si-TCP compound by osteoclasts can be detected provides a simple inexpensive format for analysis compared to the prior art techniques. The film as made in accordance with this invention, supports the biological function of bone cells. The benefit in providing the film on a transparent supporting substrate, such as quartz or glass, lends to easy evaluation techniques of the diagnostic process including automated machine reading.

Ideally the film thickness is greater than 0.1 micron because it has been found that at film thicknesses less than 0.1 microns it is difficult to obtain uniform film coverage, free from discrete voids. As to the upper thickness limit for the film, it can be of any desired thickness depending upon its end use. The degree of resorption may be detected by light transmittance, which preferably requires a film less than 10 microns in thickness. The substrate is of quartz which readily withstands the required sintering temperatures and has the desired degree of transparency to permit light transmittance tests to determine the extent of resorption of the film material.

The developed thin films may be used in kits and analytical products to provide for assessment of bone cell activity. The film may be embodied in the form of a kit or device comprising quartz substrates, pre-coated with the stabilized calcium phosphate (Si-TCP) compound, which may be used in a cell culture vessel (possibly a 24-well optionally sterilized multi-well plate i.e. of approximately 15 mm diameter) as a system suitable for the culture of mixed bone cell populations. The device is simple and relies on only routine laboratory equipment and techniques for use, is suitable for quantitative analysis, and is inexpensive to fabricate but strong enough to withstand normal levels of handling and may be packaged in lots, of (for example) 24 samples in a plastic multiwell plate. The thin film surfaces have a defined and reproducible chemistry and are mechanically strong enough to withstand transport when used with an appropriate packing material.

In each case the culture conditions may be such that osteoclasts, in either mononuclear or multinucleate form could be expected to survive in a functional state and resorb the synthetic stabilized calcium phosphate compound. Similarly, osteoblasts are also capable of actively secreting mineralized matrix under such culture conditions.

Once the colloidal suspension (sol-gel) is prepared, it may be applied as a thin film to the desired substrate in a variety of techniques. For example, the dip-coating method (C. J. Brinker et al., Fundamentals of Sol-Gel Dip Coating, Thin Solid Films, Vol. 201, No. 1, 97–108, 1991) consists of a series of processes: withdrawal of the substrate from a sol-gel or solution at a constant speed, drying the coated liquid film at a suitable temperature, and firing the film to a final ceramic.

In spin-coating the sol-gel is dropped on a plate which is rotating at a speed sufficient to distribute the solution uniformly by centrifugal action. Subsequent treatments are the same as those of dip coating.

It is appreciated that there are a variety of other techniques which may be used to apply a thin film of the sol-gel to the substrate. Other techniques include a spraying of the sol-gel, roller application of the sol-gel, spreading of the sol-gel and painting of the sol-gel.

An alternative to coating discrete discs of a singular size is to coat an enlarged substrate with a film of the sol-gel. The entire film on the substrate is then sintered. A device, such as a grid, may then be applied over the film to divide it into a plurality of discrete test zones.

In these various techniques of the sol-gel substance application, the thickness and quality (porosity, microstructure, crystalline state and uniformity) of formed films are affected by many factors. These include the physical properties, composition and concentration of the starting sol, the cleanliness of the substrate surface, withdrawal speed of the substrate and the firing temperature. In general the thickness depends mainly on the withdrawal rate and sol viscosity for a dip coating process. Since heterogeneity in the sol-gel is responsible for the formation of voids, the coating operation should be undertaken in a clean room to avoid particulate contamination of the sol. At the heat-treatment stage, high temperatures are required to develop the required microstructure and desired conversion of hydroxyapatite into the biomaterial (Skelite™) compound.

The purpose of applying the dip coating method to fabricate calcium phosphate films is twofold: (a) to make films with required qualities (uniformity, thickness, porosity, etc.); and (b) to make translucent Si-TCP films on transparent substrates for biological experiments.

Macroporous Structures

Figure 23:
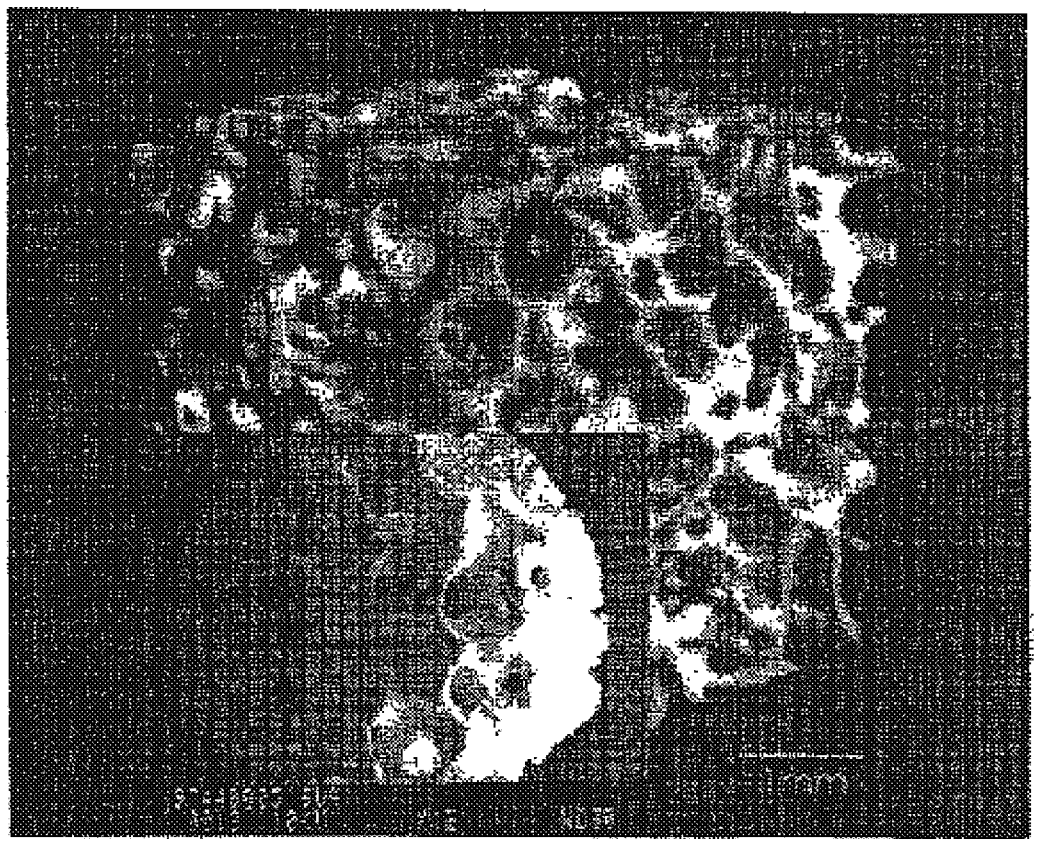
FIG. 23 is a micro CT image of natural bone architecture with inset SEM micrograph of a macroporous structure formed from the Skelite™ biomaterial compound.

A particular aspect of ceramic preparation for use in biological applications is the fabrication of ceramic pieces with a globular morphology and internal microporosity which leads to bioactivity, and a larger internal macrostructure of pores of dimensions 50–1000 $\mu$m. This encourages bone growth and subsequent remodeling in a system more closely resembling physiological in vivo bone (FIG. 23). Such macroporosity at the low end of the range being particularly suited to in vivo applications desiring rapid ingrowth of bone matrix, while macroporosity at the high end of the range allows cells in culture to access the interior for uses such as for ex vivo tissue engineering production of bone grafts.

Using powders with the prefered additive, silicon, and sintered prior to use, porous ceramics can be made as described herein in the Examples. The procedures described in the accompanying examples result in the formation of a bulk ceramic having a globular microporous structure, an underlying internal microporous structure and an internal macroporous structure allowing cells to migrate and function throughout the entire bulk ceramic unit.

It is to be understood by those skilled in the art that several different materials and procedures may be used to develop macroporosity within the ceramic structure. Other materials which are capable of pyrolysis at temperatures below the normal sintering temperatures are also useful to form the macroporous structure. The materials used should also not leave any toxic residues. It is also understood that other methods can also be used to form the macrostructure such as mechanical drilling of holes, the use of lasers or use of foaming agents.

All of the applications in which the present synthetic biomaterial compound can be used have the advantage that both osteoclasts and osteoblasts function actively with the compound in any form thus providing natural cell-mediated remodeling much like that found in vivo. The synthetic biomaterial compound of the present invention promotes both osteogenesis and resorption so that normal tissue healing can occur while simultaneously allowing the synthetic material to be resorbed in the process of normal bone tissue remodeling.

EXAMPLES

The examples are described for the purposes of illustration and are not intended to limit the scope of the invention. The examples exemplify aspects of the invention for providing a Skelite™ compound which is an additive stabilized structure having unique physical characteristics and is fully biocompatible with natural bone tissue.

Methods of synthetic chemistry and organic chemistry referred to but not explicitly described in this disclosure and examples are reported in the scientific literature and are well known to those skilled in the art.

Example 1

Preparation of Ca—P Colloidal Suspension (Sol-Gel)

The following procedure is based on preparing sufficient sol-gel hydroxyapatite for manufacturing purposes. Solution A comprises a calcium nitrate tetrahydrate and Solution B comprises an ammonium dihydrogen orthophosphate (mono basic). Solution A is mixed with Solution B to produce the desired colloidal suspension. Solution A is prepared by adding 40 mls of doubly distilled water to 4.722 grams of calcium nitrate, $Ca(NO_3)_2$. The solution is stirred at moderate speed for sufficient time to dissolve all of the calcium nitrate which is normally in the range of 3 minutes. To this solution, 3 mls of ammonia hydroxide ($NH_4OH$) is added and stirred for approximately another 3 minutes. To this solution is added 37 mls of double distilled water to provide a total solution volume of approximately 80 mls. The solution is stirred for another 7 minutes and covered. The pH of the solution is tested where a pH of about 11 is desired.

Solution B is prepared by adding 60 mls of double distilled water to a 250 ml beaker containing 1.382 grams of $NH_4H_2PO_4$. The beaker is covered and stirred at moderate speed for 3 to 4 minutes until all $NH_4H_2PO_4$ is dissolved. To this solution is added 71 mls of $NH_4OH$ and the beaker then covered and stirring continued for approximately another 7 minutes. To this is added another 61 mls of double distilled water and the beaker covered to provide a total solution volume of approximately 192 mls. The solution is then stirred for a further 7 minutes and covered. The pH of the solution is tested where a pH of about 11 is desired.

The desired sol-gel is then prepared by combining Solution B with Solution A. All of Solution A is introduced to a 500 ml reagent bottle. Stirring is commenced at a moderate speed and Solution B introduced to the reagent bottle at a rate of approximately 256 mls per hour until all 192 ml of Solution B is delivered into Solution A. An excess of Solution B may be prepared to compensate for any solution losses which may occur in the transfer process. After completion of this addition and combination of Solution A with Solution B, the resultant product is continued to be stirred at moderate speed for approximately 24 hours. The resultant colloidal suspension (sol-gel) is inspected for any abnormal precipitation or agglomeration. If any abnormal precipitation or agglomeration has occurred, the solution must be discarded and preparation commenced again. Approximately 240 mls of the colloidal suspension, that is the resultant sol-gel, is delivered to a centrifuge bottle and centrifuged for 20 minutes at about 500 rpm at room temperature. Following centrifugation, 180 mls of supernatant is discarded without disturbing the sediments. The sediments are gently resuspended by mixing in a smooth rotating manner for about 30 minutes.

The resulting Ca—P colloidal suspension may be used in a variety of further preparations.

Example 2

Sintering of Ca—P Products

The following sintering process may be carried out in standard laboratory furnaces of various sizes, capable of operating at temperatures from ambient up to at least 1100° C., and designed to maintain accurate and stable internal temperatures, particularly between 800° C. and 1100° C., such as Lindberg models 51744 or 894-Blue M. The components prepared by any of the procedures described herein are carefully transferred onto a standard ceramic plate (as is common practice in the Lindberg oven). The ceramic plate is used as a carrier during the sintering process to facilitate easy loading and withdrawal of multiple substrates from the furnace. The furnace temperature is set to the temperature required to achieve the desired ratios of HA:SiTCP. Utilizing a programmable furnace such as the Lindberg model 894-Blue M, the furnace may be programmed to hold the desired temperature, which will normally be selected from the range 800° C. to 1100° C., for a maximum of one hour to ensure desired diffusion of the selected stabilizing additives. The ceramic plate carrying the sintered substrates is removed at any time after the internal furnace temperature has cooled to an acceptable and safe touch-temperature of approximately 60° C. Individual substrates may then be stored or packaged for final use.

In accordance with this process a fine or coarse powder, pellets, three-dimensional shaped pieces, macroporous structures, thin films and coatings of the biomaterial compound can be produced on a consistent basis having the desired composition where variability in the various processing parameters have been minimized to ensure such consistency.

Example 3

Preparation of Thin Films

To create a thin film on a transparent substrate, quartz (amorphous silica) substrates were cleaned using water and chromic acid and subsequently dip coated in the colloidal suspension of Example 1. The substrate needs to be thoroughly cleaned to ensure satisfactory film coverage. In the case of quartz substrates, cleaning is achieved by placing the discs in a glass beaker and supplying chromic acid cleaning solution to the glass beaker to cover all discs. The beaker is then covered. The discs are then sonicated in a water bath for 1 hour. The acid is washed away using tap water for 20 minutes. The residual tap water is removed by three changes of doubly distilled water. After the final change of double distilled water, every single disc is dried with lint-free towel and inspected for flaws in the quartz surface. Any residual particulate on the surface is removed as needed with compressed nitrogen or air. The discs are stored in covered trays in an aseptic environment. This method can be used to clean any type of quartz substrate.

Dip coating was achieved by suction mounting the substrates on a computer controlled linear slide. The mounted substrates were lowered into the colloidal suspension and immediately withdrawn at a programmed speed of 2 mm/s. Following dip coating, the substrates were allowed to dry in ambient conditions and were subsequently sintered in a programmable furnace for a period of 1 hour at temperatures ranging from 800° C. to 1100° C. The sintered thin films had a uniform translucent appearance characteristic of a polycrystalline thin film. The thin film had an approximate thickness of 0.5 to 1.0 $\mu$m with a particle size on the order of 0.2 to 1.0 $\mu$m.

Example 4

Preparation of Ca—P Powder with no Introduced Additives

Following the procedures for the formation and aging of the colloidal suspension of Example 1, the colloid was processed to the stage of reducing the volume by centrifugation. The precipitate was dried for approximately 5 hours at 100° C. and sintered for one hour in an open alumina crucible in air at a temperature of 1000° C. A fine powder was formed through mechanical grinding of the sintered material in a motorized mortar and pestle (Retsch Model RM 100 USA).

Example 5

Preparation of Ca—P Powder with Silicon as the Introduced Additive

Following the procedures for the formation and aging of the colloidal suspension of Example 1, the colloid was processed to the stage of reducing the volume by centrifugation. In order to retain the colloidal sol characteristics, the silicon additive was introduced as a sol-gel metal-organic precursor in an organic carrier. The precursor was either tetrapropyl orthosilicate ($Si(OC_3H_7)_4$ or TPOS) or tetraethyl orthosilicate ($Si(OC_2H_5)_4$ or TEOS). Addition was accomplished by creating a sol using a precursor carrier such as 2-methoxyethanol ($CH_3OCH_2CH_2OH$ or 2Me) or 2-4 pentanedione ($CH_3COCH_2COCH_3$ or ACAC). The action of the carrier was to ensure that the additive did not precipitate upon addition to an aqueous solution having a pH similar to that of the Ca—P colloidal suspension. This ensured that the additive was uniformly mixed within the colloid to create a single precipitate rather than two distinct precipitates. Precipitation of the additive was examined in a separate experiment with aqueous solutions. For the silicon compounds, precipitation was minimal for 2Me, ACAC and even if no carrier was employed. The precipitate with introduced silicon was dried for approximately 5 hours at 100° C. and sintered for one hour in an open alumina crucible in air at a temperature of 1000° C. A fine powder was formed through mechanical grinding of the sintered material in a motorized mortar and pestle (Retsch Model RM 100 USA). The presence of the additive within the sintered ceramics was checked by wet chemical analysis.

Example 6

Preparation of Ca—P Powder with Silicon (In the Form of a Colloidal Suspension) as the Introduced Additive As an alternative to the process defined in Example 5 involving the use of a silicon additive in the form of a sol-gel metal-organic precursor in an organic carrier, a different delivery mechanism for silicon was utilized where silica was added to the Ca—P colloid by way of a finely divided (~10–1100 nm) fumed silica colloid (Cab-o-Sperse™, Cabot Corporation). This approach expands the flexibility of the manufacturing process while providing for intimate mixing between the Ca—P colloid and the silica colloid.

The Ca—P colloid, with the silica colloid added, was subsequently sprayed into powder using a Yamato-Ohkawara DL-41 spray dryer. The powder was then sintered using a heating profile based on a ramp rate of 5° C./min., dried at 200° C. for about 180 mins, calcined at 550° C. for about 60 mins, then sintered at 1000° C. for about 60 mins. The presence of the additive within the sintered ceramics was confirmed using wet chemical analysis.

Example 7

Preparation of Ca—P Powder with Titanium as the Introduced Additive

Following the procedures for the formation and aging of the colloidal suspension of Example 1, the colloid was processed to the stage of reducing the volume by centrifugation. In order to retain the colloidal sol characteristics, the titanium additive was introduced as a sol-gel metal-organic precursor in an organic carrier. The precursor was titanium n-propoxide ($Ti(OC_3H_7)_4$). Addition was accomplished by creating a sol using a precursor carrier such as 2-methoxyethanol ($CH_3OCH_2CH_2OH$ or 2Me) or 2-4 pentanedione ($CH_3COCH_2COCH_3$ or ACAC). ACAC was used in particular for its strong chelating action. Precipitation of the additive was examined in a separate experiment with aqueous solutions. For titanium n-propoxide, precipitation of the additive occurred for both no carrier and 2Me, but not for ACAC. The precipitate with introduced titanium was dried for approximately 5 hours at 100° C. and sintered for one hour in an open alumina crucible in air at a temperature of 1000° C. A fine powder was formed through mechanical grinding of the sintered material in a motorized mortar and pestle (Retsch Model RM 100 USA). The presence of the additive within the sintered ceramics was checked by wet chemical analysis.

Example 8

Preparation of Ceramic Pellets

Ceramic pellets were formed from previously sintered powder that had been prepared according to Examples 4, 5, or 6, using a small amount of the concentrated colloid suspension mixed into the sintered powder as a binding agent. The powders were uniaxially pressed into pellets with a pressure of $1 \times 10^8$ N/m² [15,000 psi]. The final pellets were sintered for one hour in air at a temperature of 1000° C. to create ceramic components with the desired characteristics. Following thermal processing, the pellet density was approximately 1.5 g/cm³, and the pellet exhibited a uniform microporosity throughout the structure.

Example 9

Preparation of Macroporous Structures

Sintered powder that had been prepared according to Examples 4, 5, or 6, was sieved using a motorized sieve shaker (Retsch Model AS200 BASIC USA). Powder having a particle size of—325 Mesh was collected and subsequently suspended in water to form a slurry. The interior and exterior surfaces of a preformed piece of open cell (reticulated) polyurethane foam were completely coated by immersing the foam in the slurry. The slurry-coated component was then allowed to dry and was subsequently sintered at 1000° C. for 1 hour. During thermal processing, the foam was removed from the structure through pyrolysis. Importantly, the shape of the final ceramic component replicates the original shape of the foam, including the open-cell structure.

In the preparation of these components, the pore density of the foam was selected to produce the required pore size in the ceramic. Typical pore sizes prepared were in the range of 45 to 80 pores per inch. The coating of the foam was managed to ensure complete coverage of the foam without clogging of the cells. The duration and temperature of the thermal processing were selected to ensure pyrolysis of the foam and to obtain the desired physical properties of the resulting macroporous structure.

An alternate method for the formation of a macroporous structure is to introduce styrene balls of a desired size into the powder being prepared according to Examples 4, 5 or 6. The mixture is combined with a binder, such as a PVA (polyvinyl alcohol) solution, and uniaxially pressed into pellets. A pressing pressure of $1 \times 10^8$ N/m² [15,000 psi] was selected so as to not extrude the styrene during compression. The pellets were subsequently sintered at 1000° C. for one hour during which the styrene was removed through pyrolysis.

Example 10

Preparation of Drug Carrier with Associated Pharmaceutical Agent

Depending on application requirements, either the powder of Example 5 or the macroporous structure of Example 9 was sterilized using ethylene oxide or similar approved medical device sterilization technique. In a laminar flow hood, a liquid drug volume was made up according to dosing requirements. In the case of the agent BCSF™ (Bone Cell Stimulating Factor), this required addition of sterile normal saline (0.9% NaCl) to previously lyophilized stored aliquots of the drug, at room temperature. Following reconstitution, the drug was either mixed by gentle agitation with the powder, or slowly dispensed over the surface of the macroporous structure.

Recognizing the natural protein avidity of the bioceramic material, a period of 5 minutes was allowed for the drug to percolate and bind to either the powder or the macroporous structure. Following this period, the preparation was ready for direct patient administration as a therapeutic device or for use as a tissue-engineering scaffold.

In the case of therapeutic administration of the powder-based preparation, a predetermined volume of the suspension (powder plus attached pharmaceutical agent) was injected percutaneously at the desired skeletal site.

In the case of therapeutic administration of macroporous structures, surgical intervention was required to implant the device at skeletal sites in order to effect subsequent bone repair.

Example 11

Commercial Reference Materials

The commercially available HA (cHA), α-TCP, β-TCP, calcium silicate and silica materials listed in Table 1 (below) were used as reference standards for the analytical tech niques performed in the evaluation of the internally prepared mHA and Si-mHA materials described in this study.

TABLE 1

List of Materials Used For Experimental Samples and Reference Standards

| Commercial Materials | | Source |
|---|---|---|
| Commercial HA | cHA | Aldrich #28,939-6 Lot#04302TQ |
| α-TCP | α-TCP | Supelco Inc #3-3910 Lot#200792 |
| β-TCP | β-TCP | Fluka #21218 Analysis#357352/1 14996 |
| Calcium silicate | CaSiO$_3$ | Aldrich #37,266-8 Lot#00714LN |
| Silica | SiO$_2$ | PPG Industries Inc. #63231674 Lot#9-134 |
| Microporous HA | mHA | Powder prepared from the thermal processing of the colloid in equation (1) |
| Si-TCP + mHA | Si-mHA | Powder prepared from the thermal processing of the colloid in equation (1) where Si is the introduced additive |

Example 12

Analytical Techniques

X-ray diffraction (XRD) spectra of thin films were acquired using a glancing angle (GA-XRD) technique with an angle of incidence θ=2°, whereas powders were examined using conventional θ-2θ geometry. The source was a 12 kW Rigaku rotating anode XRD generator fitted with a Cr target for improved peak resolution. The glancing angle geometry significantly reduced the contribution from the substrate. For convenience of comparison to other literature, all spectra were converted to that expected for a Cu anode using the following relationship: $\sin(\theta_{Cu})=(\lambda_{Cu}/\lambda_{Cr})\sin(\theta_{Cr})$, where $\lambda_{Cu}=1.54056$ Å and $\lambda_{Cr}=2.28970$ Å. The phase composition was determined by comparing acquired spectra with peaks identified in the Joint Committee on Powder Diffraction Standards (JCPDS) database of standards [20]. Of particular relevance to this study are the XRD spectra of HA (JCPDS #9-432), α-TCP (JCPDS #9-348) and β-TCP (JCPDS #9-169). Following the collection of XRD data, the background noise was subtracted and the integrated intensities of peaks distinguishable as HA, α-TCP or β-TCP were calculated. These values were then used to determine the percentage phase composition (plus or minus 5%).

Optical microscopy, scanning electron microscopy (SEM, using a JEOL JSM 840) and transmission electron microscopy (TEM, using a Philips CM20) were performed to assess the surface and bulk morphology. Chemical analysis of the samples was carried out by wet chemical methods and neutron activation analysis. Wide-line nuclear magnetic resonance (NMR) experiments on $^{29}$Si were accomplished using a Bruker NMR CXP 200 MHz spectrometer with magic angle spinning using a pulse width of 5 ms and a pulse delay of 20 s. Infrared spectroscopy (IR) of powders using a KBr pellet technique utilized a BOMEM MB-120 spectrometer. Approximately 2 mg of sample and approximately 200 mg of KBr were ground and pressed in a 6 mm diameter die at 10 tonnes for 1 minute to produce uniform discs for analysis.

A particle size analysis of the Ca—P colloid at various stages of processing was made by observation of 633 nm He—Ne laser light scattered at various angles. Samples were prepared by adding 10 drops of the precipitated solution to 4 mL ammoniated water (one part 30% NH$_4$OH mixed with five parts water) having a pH greater than 10. Results from these suspensions were reproducible for equivalent samples and stable over time. The power spectrum of the scattered light at a known angle was fitted to a Lorentzian distribution and analyzed by standard methods using a solution viscosity of $8.9 \times 10^4$ kg m$^{-1}$s$^{-1}$ and refractive index of 1.3312 (Clark, N., H. Lunacek and G. Benedek. *Am J Phys* 38(5) 1970; pp. 575–85 and Schumacher, R. *Am J Phys* 54(2) 1986; pp. 137–41).

Although preferred embodiments have been described herein in detail, it is understood by those skilled in the art that variations may be made thereto without departing from the scope of the invention as defined by the appended claims.

TABLE 2

Summary of Effective Ionic Radius and Ionic Crystal Radius for Various Elements
Data from: Shannon, R. D., Acta Cryst. (1976) A32, 751

| Ion | Coordination Number (CN) | Ionic Crystal Radius (CR) | Effective Ionic Radius (IR) |
|---|---|---|---|
| B$^{3+}$ | 4 | 0.25 | 0.11 |
|  | 6 | 0.41 | 0.27 |
| Ba$^{2+}$ | 6 | 1.49 | 1.35 |
|  | 8 | 1.56 | 1.42 |
| Ca$^{2+}$ | 6 | 1.14 | 1.00 |
|  | 8 | 1.26 | 1.12 |
| Ce$^{3+}$ | 6 | 1.15 | 1.01 |
|  | 8 | 1.28 | 1.14 |
| La$^{3+}$ | 6 | 1.17 | 1.03 |
|  | 8 | 1.30 | 1.16 |
| Mg$^{2+}$ | 4 | 0.71 | 0.57 |
|  | 6 | 0.86 | 0.72 |
|  | 8 | 1.03 | 0.89 |
| P$^{5+}$ | 4 | 0.31 | 0.17 |
|  | 6 | 0.52 | 0.38 |
| Sc$^{3+}$ | 6 | 0.89 | 0.75 |
|  | 8 | 1.01 | 0.87 |
| Si$^{4+}$ | 4 | 0.40 | 0.26 |
|  | 6 | 0.54 | 0.40 |
| Ti$^{4+}$ | 4 | 0.56 | 0.42 |
|  | 6 | 0.75 | 0.61 |
|  | 8 | 0.88 | 0.74 |
| Y$^{3+}$ | 6 | 1.04 | 0.90 |
|  | 8 | 1.16 | 1.02 |
| Zr$^{4+}$ | 4 | 0.73 | 0.59 |
|  | 6 | 0.86 | 0.72 |
|  | 8 | 0.98 | 0.84 |

We claim:

1. A method for the production of a calcium phosphate biomaterial powder, the method comprising:
   (a) mixing a silica colloid with a calcium phosphate colloidal suspension;
   (b) spray drying (a) into powder;
   (c) sintering said powder.

2. The method of claim 1, wherein said silica colloid is finely divided fumed silica colloid.

3. The method of claim 2, wherein said calcium phosphate colloidal suspension is precipitated from a mixture of calcium nitrate tetrahydrate and ammonium dihydrogen orthophosphate.

4. The method of claim 3, wherein sintering is conducted using a heating profile with a ramp rate of about 5° C./minute, drying at about 200° C. for about 180 minutes, calcining at about 550° C. for about 60 minutes, and sintering at about 1000° C. for about 60 minutes.

5. The method of claim 4, wherein said powder is formed into three dimensional pieces.

6. The method of claim 5, wherein said powder has up to about 10 weight percent of silicon.

7. A powdered calcium phosphate biomaterial produced by the method of claim 1.

8. A method for the production of a calcium phosphate biomaterial powder, the method comprising:

(a) mixing a solution of calcium nitrate tetrahydrate with a solution of ammonium dihydrogen orthophosphate to produce a calcium phosphate colloidal suspension;

(b) mixing (a) with a finely divided fumed silica colloid;

(c) spray drying (b) into a powder; and (d) sintering using a heating profile with a ramp rate of about 5° C. per minute, drying at about 200° C. for about 180 minutes, calcining at about 550° C. for about 60 minutes and sintering at about 1000° C. for about 60 minutes.

9. A powdered calcium phosphate biomaterial produced by the method of claim 8.

10. The method of claim 8, wherein said calcium phosphate colloidal suspension is centrifuged to reduce the volume prior to the addition of said finely divided fumed silica colloid.

11. The method of claim 2 or 8, wherein said finely divided silica colloid has a particle size of about 10–100 nm.

* * * * *